US010297699B2

(12) United States Patent
Meyer et al.

(10) Patent No.: US 10,297,699 B2
(45) Date of Patent: May 21, 2019

(54) IN-PLANE RESONANT-CAVITY INFRARED PHOTODETECTORS WITH FULLY-DEPLETED ABSORBERS

(71) Applicant: The United States of America, as represented by the Secretary of the Navy, Washington, DC (US)

(72) Inventors: Jerry R. Meyer, Catonsville, MD (US); Igor Vurgaftman, Severna Park, MD (US); Chadwick Lawrence Canedy, Washington, DC (US); William W. Bewley, Falls Church, VA (US); Chul Soo Kim, Springfield, VA (US); Charles D. Merritt, Fairfax, VA (US); Michael V. Warren, Arlington, VA (US); Mijin Kim, Springfield, VA (US)

(73) Assignee: The United States of America, as represented by the Secretary of the Navy, Washington, DC (US)

( * ) Notice: Subject to any disclaimer, the term of this patent is extended or adjusted under 35 U.S.C. 154(b) by 0 days.

(21) Appl. No.: 15/924,385

(22) Filed: Mar. 19, 2018

(65) Prior Publication Data
US 2018/0212080 A1    Jul. 26, 2018

Related U.S. Application Data

(63) Continuation-in-part of application No. 15/605,996, filed on May 26, 2017, now Pat. No. 10,062,794.
(Continued)

(51) Int. Cl.
H01L 31/0232 (2014.01)
G01N 21/00 (2006.01)
(Continued)

(52) U.S. Cl.
CPC ....... *H01L 31/02327* (2013.01); *G01N 21/00* (2013.01); *G01N 21/552* (2013.01);
(Continued)

(58) Field of Classification Search
CPC .................... H01L 31/02327; G01N 21/00
(Continued)

(56) References Cited

U.S. PATENT DOCUMENTS 5,793,787 A    8/1998 Meyer et al.
6,013,912 A    1/2000 Pautrat et al.
(Continued)

FOREIGN PATENT DOCUMENTS

EP    1577959 A2    9/2005

OTHER PUBLICATIONS

G.-H. Duan et al., "Hybrid III—V on Silicon Lasers for Photonic Integrated Circuits on Silicon," IEEE J. Sel. Topics Quant. Electron 20, 6100123 (2014).
(Continued)

*Primary Examiner* — Igwe U Anya
(74) *Attorney, Agent, or Firm* — US Naval Research Laboratory; Joslyn Barritt

(57) ABSTRACT

Resonant-cavity infrared photodetector (RCID) devices that include a thin absorber layer contained entirely within the resonant cavity. In some embodiments, the absorber is a single type-II InAs-GaSb interface situated between an AlSb/InAs superlattice n-type region and a p-type AlSb/GaSb region. In other embodiments, the absorber region comprises quantum wells formed on an upper surface of the n-type region. In other embodiments, the absorber region comprises a "W"-structured quantum well situated between two barrier layers, the "W"-structured quantum well comprising a hole quantum well sandwiched between two electron quantum wells. In other embodiments, the RCID
(Continued)

includes a thin absorber region and an nBn or pBp active core within a resonant cavity. In some embodiments, the RCID is configured to absorb incident light propagating in the direction of the epitaxial growth of the RCID structure, while in other embodiments, it absorbs light propagating in the epitaxial plane of the structure.

11 Claims, 20 Drawing Sheets

Related U.S. Application Data

(60) Provisional application No. 62/342,260, filed on May 27, 2016.

(51) Int. Cl.
| | |
|---|---|
| *H01L 31/105* | (2006.01) |
| *H01L 31/0304* | (2006.01) |
| *H01L 31/109* | (2006.01) |
| *G02B 6/124* | (2006.01) |
| *G02B 6/12* | (2006.01) |
| *G01N 21/552* | (2014.01) |
| *G01N 21/3504* | (2014.01) |
| *G01N 21/77* | (2006.01) |

(52) U.S. Cl.
CPC ......... *G02B 6/12004* (2013.01); *G02B 6/124* (2013.01); *H01L 31/03046* (2013.01); *H01L 31/105* (2013.01); *H01L 31/109* (2013.01); *G01N 21/3504* (2013.01); *G01N 21/7746* (2013.01); *G02B 2006/12061* (2013.01); *G02B 2006/12078* (2013.01); *G02B 2006/12123* (2013.01); *G02B 2006/12138* (2013.01)

(58) Field of Classification Search
USPC ........................................................ 257/432
See application file for complete search history.

(56) References Cited

U.S. PATENT DOCUMENTS

| | | | |
|---|---|---|---|
| 9,209,601 B2 | 12/2015 | Davies et al. | |
| 9,362,428 B2* | 6/2016 | Chen | H01L 31/0232 |
| 9,612,398 B2 | 4/2017 | Vurgaftman et al. | |
| 9,923,338 B2 | 3/2018 | Meyer et al. | |
| 2002/0030198 A1 | 3/2002 | Coman et al. | |
| 2009/0127462 A1 | 5/2009 | Gunapala et al. | |
| 2013/0301668 A1* | 11/2013 | Zhang | H01S 5/323 |
| | | | 372/50.1 |
| 2014/0029085 A1* | 1/2014 | Bond | H01S 5/10 |
| | | | 359/346 |
| 2015/0214425 A1* | 7/2015 | Taylor | H01S 5/0421 |
| | | | 385/14 |
| 2017/0373472 A1 | 12/2017 | Meyer et al. | |

OTHER PUBLICATIONS

A. Spott et al., "Heterogeneous Integration for Mid-Infrared Silicon Photonics," IEEE J. Sel. Topics Quant. Electron. 23, 8200818 (2017).
P. Ma et al., "Low-loss chalcogenide waveguides for chemical sensing in the mid-infrared," Opt. Expr. 21, 29927 (2013).
B. Schwarz et al., "Monolithically integrated mid-infrared lab-on-a-chip using plasmonics and quantum cascade structures," Nat. Commun. 5, 4085 (2014).
S.-H. Hsu, "Reflectively Coupled Waveguide Photodetector for High Speed Optical Interconnection," Sensors 10, 10863 (2010).
A. W. Fang et al., "Integrated AlGaInAs-silicon evanescent racetrack laser and photodetector," Opt. Expr. 15, 2315 (2007).
M. Muneeb et al., "III-V-on-silicon integrated micro—spectrometer for the 3 μm wavelength range," Opt. Expr. 24, 9465 (2016).
R. Wang et al., "III-V-on-Silicon Photonic Integrated Circuits for Spectroscopic Sensing in the 2-4 μm Wavelength Range," Sensors 17, 1788 (2017).
M. J. R. Heck et al., "Hybrid Silicon Photonic Integrated Circuit Technology," IEEE JSTQE: Semiconductor Lasers (2013).
C. S. Kim et al., "Improved Mid-Infrared Interband Cascade Light Emitting Devices," Opt. Engr. 57, 011002 (2018).
W. Zhou et al, "Monolithically, widely tunable quantum cascade lasers based on a heterogeneous active region design," Scientific Reports 6, 25213 (2016).
M. Ariga et al., "Low Threshold GaInAsP Lasers with Semiconductor/Air Distributed Bragg Reflector Fabricated by Inductively Coupled Plasms Etching," Jpn. J. Appl. Phys. 39, 3406 (2000).
M. Okuda et al., Tunability of Distributed Bragg-Reflector Laser by Modulating Refractive Index in Corrugated Waveguide, Jpn. J. Appl. Phys. 16, 1501 (1977).
J.G.A. Wehner et al., "Resonant Cavity-Enhanced Mercury Cadmium Telluride Detectors," Journal of Electronic Materials, vol. 33, No. 6, 2004, pp. 604-608.
L. Jun et al., "Design of a resonant-cavity-enhanced GaInAsSb/GaSb photodetector," Sem. Sci. Technol. 19, 690 (2004).
M. Arnold et al., "Lead salt mid-IR photodetectors with narrow linewidth," J. Cryst. Growth 278 (2005) 739-742.
F. Felder et al., "Tunable lead-chalcogenide on Si resonant cavity enhanced midinfrared detector," Appl. Phys. Lett. 91, 101102 (2007).
F. Felder et al., "Lead Salt Resonant Cavity Enhanced Detector with MEMS Mirror," Phys Proc. 3 (2010) 1127-1131 ("Felder 2010").
J. Wang et al., "Resonant-cavity-enhanced mid-infrared photodetector on a silicon platform," Optics Express, vol. 18, No. 12, 12890-12896 (2010).
J. Wang et al., "Monolithically integrated, resonant-cavity-enhanced dual-band mid-infrared photodetector on silicon," Appl. Phys. Lett. 100, 211106 (2012).
Y. Shi et al., "Resonant Cavity Enhanced Heterojunction Phototransistors Based on GaInAsSb—AlGaAsSb Grown by Molecular Beam Epitaxy," IEEE Phot. Tech. Lett., vol. 10, No. 2, 258-260 (1998).
A.M. Green et al., λ ≈ 3 μm InAs resonant-cavity-enhanced photodetector, Semicond. Sci. Technol. 18 (2003) 964-967.
A.M. Green et al., "Resonant-cavity-enhanced photodetectors and LEDs in the mid-infrared," Physica E 20 (2004) 531-535.
P. Martyniuk et al., "New concepts in infrared photodetector designs," Appl. Phys. Rev. 1, 041102 (2014).
M. Selim Ünlü et al., "Resonant Cavity Enhanced Photonic Devices," J. Appl. Phys. 78, 607 (1995).
I. Vurgaftman, E. H. Aifer, C. L. Canedy, J. G. Tischler, J. R. Meyer, J. H. Warner, E. M. Jackson, G. Hildebrandt, and G. J. Sullivan, "Graded band gap for dark-current suppression in long-wave infrared W-structured type-II superlattice photodiodes," Appl. Phys. Lett. 89, 121114 (2006).
C. L. Canedy, E. H. Aifer, J. H. Warner, I. Vurgaftman, E. M. Jackson, J. G. Tischler, S. P. Powell, K. Olver, J. R. Meyer, and W. E. Tennant, "Controlling dark current in type-II superlattice photodiodes," Infrared Phys. Technol. 52, 326 (2009).
D. Lee, M. Carmody, E. Piquette, P. Dreiske, A. Chen, A. Yulius, D. Edwall, S. Bhargava, M. Zandian, and W. E. Tennant, "High-operating temperature HgCdTe: A vision for the near future," J. Electronic Materials 45, 4587 (2016).
J.R. Meyer et al., "Type-II quantum-well lasers for the mid-wavelength infrared," Appl. Phys. Lett. 67 (6), pp. 757-759 (1995).
E.H. Aifer et al., "W-structured type-II superlattice long-wave infrared photodiodes with high quantum efficiency," Appl. Phys. Lett. 89, 053519 (2006)).
D. Wang et al., "Metamorphic InAsSb-based barrier photodetectors for the long wave infrared region," Appl. Phys. Lett. 103, 051120 (2013).
J. Lu et al., "Evaluation of antimony segregation in InAs/InAs1—xSbx type-II superlattices grown by molecular beam epitaxy," J. Appl. Phys. 119, 095702 (2016).

(56) References Cited

OTHER PUBLICATIONS

S. Maimon et al., "nBn detector, an infrared detector with reduced dark current and higher operating temperature," Appl. Phys. Lett. 89, 151109 (2006).
A. Soibel et al., "Room temperature performance of mid-wavelength infrared InAsSb nBn detectors," IR Phys. Technol. 70, 121 (2015).
E. A. Plis et al., "Bias Switchable Dual-Band InAs/GaSb Superlattice Detector With pBp Architecture," IEEE Phot. J. 3, 234 (2011).
O. Dier et al., "Reduction of hetero-interface resistivity in n-type AlAsSb/GaSb distributed Bragg reflectors," Semicond. Sci. Technol. 23, 025018 (2008).
A. Bachmann et al., "Single-mode electrically pumped GaSb-based VCSELs emitting continuous-wave at 2.4 and 2.6 µm," New Journal of Physics 11, 125014 (2009).
W. W. Bewley, C. L. Canedy, C. S. Kim, C. D. Merritt, M. V. Warren, I. Vurgaftman, J. R. Meyer, and M. Kim, "Room-temperature Mid-Infrared Interband Cascade Vertical-Cavity Surface-Emitting Laser," Appl. Phys. Lett. 99, 151108 (2016).
J. Abell, C. S. Kim, W. W. Bewley, C. D. Merritt, C. L. Canedy, I. Vurgaftman, J. R. Meyer, and M. Kim, "Mid-infrared interband cascade light emitting devices with milliwatt output powers at room temperature," Appl. Phys. Lett. 104, 261103 (2014).
Search Report and Written Opinion dated Sep. 6, 2017 in corresponding PCT Application No. PCT/US2017/034608.
G. Bishop et al., "nBn detectors based on InAs/GaSb type-II strain layer superlattice," J. Vac. Sci. Technol. B 26(3) (May/Jun. 2008), pp. 1145-1148.

\* cited by examiner

IN-PLANE RESONANT-CAVITY INFRARED PHOTODETECTORS WITH FULLY-DEPLETED ABSORBERS

CROSS-REFERENCE

This Application is a Continuation-in-Part of, and claims the benefit of priority under 35 U.S.C. § 120 based on, U.S. patent application Ser. No. 15/605,996 filed on May 26, 2017, which is a Nonprovisional of, and claims the benefit of priority under 35 U.S.C. § 119 based on, Provisional Application No. 62/342,260 filed on May 27, 2016. The prior applications, all references cited therein, and all references cited in the present disclosure are hereby incorporated by reference into the present disclosure in their entirety.

TECHNICAL FIELD

The invention relates to infrared (IR) photodetectors, particularly to IR photodetectors with dramatically improved sensitivity within a chosen spectral band due to absorption enhancement by a vertical resonant cavity in which the absorber region is fully depleted of electrons and holes.

BACKGROUND

A primary figure of merit for the performance of an IR photodetector is its normalized signal-to-noise ratio, or detectivity D*. When the detectivity is dominated by the dark electrical noise, the important functional dependence is $$D^* \propto QE/\lambda J_b^{1/2}, \tag{1}$$

were QE is the device external quantum efficiency, representing the fraction of incident photons that produce an electron-hole pair that is collected to produce electrical current, $\lambda$ is the wavelength, and $J_b$ is the dark current density (in the absence of any optical signal or background) at the operating bias. If the operating bias is zero, the dark current density is replaced by $kT/R_0A$, where $R_0A$ is the resistance-area product at zero bias. The proportionality relation in Equation (1) also depends on some fundamental constants that are not affected by the device design.

Several previous works have discussed and simulated the potential advantages of resonant cavity infrared detectors (RCIDs). See J. G. A. Wehner et al., "Resonant Cavity-Enhanced Mercury Cadmium Telluride Detectors," *Journal of ELECTRONIC MATERIALS*, Vol. 33, No. 6, 2004, pp. 604-608; see also L. Jun et al., "Design of a resonant-cavity-enhanced GaInAsSb/GaSb photodetector," *Sem. Sci. Technol.* 19, 690 (2004).

RCIDs typically form a resonant cavity along the vertical axis by positioning two mirrors above and below the absorber. Thanks to the mirrors, any incident light with a wavelength tuned to the resonant mode of the cavity makes multiple passes through the absorber. This can allow a thin absorber positioned near the antinode of the cavity electric field to absorb most of the incident light for high QE, even when the absorber is much thinner than the absorption length without enhancement $(1/\alpha_0)$.

The block schematic in FIG. 1 illustrates aspects of a generic resonant-cavity detector structure according to the prior art, configured for illumination from the top side thereof by light source 110. As can be seen in FIG. 1, such a structure in accordance with the prior art includes a bottom contact layer 102 on a bottom surface of an n-type substrate 101 (or otherwise positioned below the absorber region 106), a semiconductor bottom mirror 103, an n-type region 104 and p-type region 105 (in alternative configurations the p-type region may be positioned below the absorber sand the n-type region above) with a thin absorber region 106 between the n- and p-type regions, and a dielectric top mirror 108 (which may alternatively be a second semiconductor mirror). The top and bottom mirrors 103/108 form a resonant cavity 100 that significantly enhances the net absorption for high QE even when the absorber is much thinner than the 2-10 µm required to achieve high QE in a conventional broadband detector that does not employ a resonant cavity.

In other configurations known to the art, illumination is from the substrate side. In such cases, the "bottom" contact may be formed by patterning an annular ring on the substrate side of the structure (possibly after the substrate has been removed by polishing and/or etching), and the contact metallization deposited on top of the mesa may form part of the "top" mirror.

The detector mesa (which is typically circular or square) is etched to below the active absorber region 106, and in configurations employing illumination from the top an annular top metal contact layer 109 is deposited around its perimeter. Before metallization of the top contact, the mesa sidewalls and exposed region outside the mesa and below the junction (formed by the mesa etch) are coated with a dielectric 107 such as SiN to prevent shorting of the junction.

The QE at the cavity's resonance wavelength a res is given by:

$$QE(\lambda_{res}) = \eta_c \frac{SA(1-R_1)(1+R_2)}{\left(1-\sqrt{R_1 R_2}\right)^2} \tag{2}$$

where $R_1$ and $R_2$ are the reflectivities of the top and bottom mirrors, respectively, S is the standing-wave enhancement factor that ranges from 0 to 2, depending on the position of the thin absorber with respect to the antinode of the cavity electric field, $\eta_c$ is the carrier collection efficiency, which is expected to be nearly unity for the thin absorber, and A is the absorbance per pass in the absence of the cavity. The absorbance A of a thin absorber generally has a limit of $A=\alpha_0 d$ for a bulk-like absorber that does not reside within a resonant cavity, where $\alpha_0(\lambda)$ is the absorption coefficient, and $A=M\alpha$ for an absorber comprising one or more quantum wells (QWs), where M is the number of QWs and a is a dimensionless fraction representing the absorbance per pass by a single QW.

To maximize the photon absorbance within a relatively small spectral range near the resonance peak, the reflectivity $R_2$ of the bottom mirror should be as close to unity as possible, while the reflectivity $R_1$ of the top mirror can be varied to obtain the desired tradeoff between spectral width and absorption enhancement.

When $R_1$ and $R_2$ are close to unity, the QE can be high even when the absorber is extremely thin, e.g., a single QW. Another consequence of the cavity's high finesse is that the spectral linewidth over which the absorption is strongly enhanced narrows correspondingly. The full width at half maximum (FWHM) of the QE spectral peak (in wavelength units) is:

$$\delta\lambda = \frac{\left(1-\sqrt{R_1 R_2}\right)^2}{\pi (R_1 R_2)^{1/4}} FSR \qquad (3)$$

where FSR=$\lambda_{res}^2/(2\ nL)$ is the free spectral range of the cavity, and n is the refractive index. The effective cavity length L includes both the thickness of the region between the mirrors and the penetration depths into the mirrors, which are non-negligible if the mirrors are realized as quarter-wavelength stacks.

If we further assume perfect collection of the photogenerated carriers ($\eta_c$=1) and that the thin absorber is positioned exactly at the resonant cavity's antinode (S=2), the on-resonance QE from Equation (2) and the FWHM of the spectral peak from Equation (3) become:

$$QE(\lambda_{res}) = \frac{4A(1-R_1)}{\left(1-\sqrt{R_1}\right)^2} \text{ and} \qquad (4)$$

$$\frac{\delta\lambda}{\lambda_{res}} = \frac{\left(1-\sqrt{R_1}\right)^2}{\pi R_1^{1/4}} \frac{\lambda_{res}}{2nL} \qquad (5)$$

For broadband applications such as most instances of thermal imaging, it is disadvantageous to incorporate the detector's absorber region into a resonant cavity, since the loss of signal resulting from the much narrower spectral response more than offsets the absorbance enhancement provided by the resonant cavity. However, if the signal one wishes to detect is already narrow, the employment of a resonant cavity centered on the wavelength of interest can substantially increase the detectivity D* while retaining high QE, since the dark current is minimized by the very thin absorber region. A classic example for which the RCID configuration may be advantageous is laser-based chemical sensing of a trace gas, whose unique and narrow (<<0.1 nm) infrared absorption lines provide a fingerprint for identifying the given species and quantifying its concentration.

Challenges can arise when the resonant cavity approach is extended to longer wavelengths in the shortwave infrared (SWIR), midwave infrared (MWIR), and longwave infrared (LWIR) regions. The goal is to substantially enhance the detectivity, within a narrow spectral band, over that attainable using a state-of-the-art conventional broadband IR detector. While several RCIDs operating in the MWIR have been demonstrated previously (see below), to date none has exhibited a performance level competitive with that of a state-of-the-art conventional broadband IR detector operating at the same temperature and wavelength.

To our knowledge, all of the previous attempts to exploit a resonant-cavity absorption enhancement at a wavelength beyond 2.5 µm have performed at levels well below the state-of-the-art for conventional broadband IR detectors. Most of the previous RCID demonstrations have employed the lead-salt material system. See, e.g., M. Arnold et al., "Lead salt mid-IR photodetectors with narrow linewidth," *J. Cryst. Growth* 278 (2005) 739-742; F. Felder et al., "Tunable lead-chalcogenide on Si resonant cavity enhanced midinfrared detector," *Appl. Phys. Lett.* 91, 101102 (2007) ("Felder 2007"); F. Felder et al., "Lead Salt Resonant Cavity Enhanced Detector with MEMS Mirror," *Phys Proc.* 3 (2010) 1127-1131 ("Felder 2010"); J. Wang et al., "Resonant-cavity-enhanced mid-infrared photodetector on a silicon platform," *Optics Express*, Vol. 18, No. 12, 12890-12896 (2010); and J. Wang et al., "Monolithically integrated, resonant-cavity-enhanced dual-band mid-infrared photodetector on silicon," *Appl. Phys. Lett.* 100, 211106 (2012).

However, conventional lead-salt IR detector materials generally suffer from short Shockley-Read lifetimes and high unintentional background doping levels, as compared to state-of-the-art HgCdTe and III-V IR detector materials. It is therefore not surprising that resonant-cavity lead-salt detectors are limited by similar materials-related issues. HgCdTe-based resonant-cavity designs have been proposed, see J. G. A. Werner et al., "Resonant Cavity-Enhanced Mercury Cadmium Telluride Detectors," *J. Electron. Mat.* 33, 604 (2004), but to our knowledge have not been put into practice. Moreover, a monolithic semiconductor mirror technology suitable for a HgCdTe RCID has yet to be developed.

The III-V demonstrations to date have employed thick bulk absorber regions (typically d≈1 µm), which precluded significant enhancement of the detectivity. See Y. Shi et al., "Resonant Cavity Enhanced Heterojunction Phototransistors Based on GaInAsSb-AlGaAsSb Grown by Molecular Beam Epitaxy," *IEEE Phot. Tech. Lett.*, Vol. 10, No. 2, 258-260 (1998); A. M. Green et al., λ≈3 µm InAs resonant-cavity-enhanced photodetector," *Semicond. Sci. Technol.* 18 (2003) 964-967; and A. M. Green et al., "Resonant-cavity-enhanced photodetectors and LEDs in the mid-infrared," *Physica E* 20 (2004) 531-535. Since they also employed cavities with relatively low front-mirror reflectivity ($R_1$<<1), those devices should be viewed as proof-of-concept demonstrations that were never intended to advance state-of-the-art performance.

In addition, some enhancement may, in fact, be achievable using conventional III-V bulk (e.g., InAs and InAsSb) or superlattice (e.g., InAs-Ga(In)Sb and InAs—InAsSb) absorbers in p-n junction or barrier (nBn and pBp) configurations from the prior art. See P. Martyniuk et al., "New concepts in infrared photodetector designs," *Appl. Phys. Rev.* 1, 041102 (2014).

Because the resonant cavity configuration provides a strong enhancement of the net absorption over that resulting from a single pass of the light through the absorber, the absorber thickness can be shrunk to as little as ≈10 nm (e.g., a single QW) without sacrificing QE at the resonant wavelength. Therefore, because the dark current is reduced proportionally, the resonant cavity configuration will either provide higher detectivity D* at a given operating temperature, or maintain a target D* at higher operating temperature than is attainable using a conventional broadband IR detector.

SUMMARY

This summary is intended to introduce, in simplified form, a selection of concepts that are further described in the Detailed Description. This summary is not intended to identify key or essential features of the claimed subject matter, nor is it intended to be used as an aid in determining the scope of the claimed subject matter. Instead, it is merely presented as a brief overview of the subject matter described and claimed herein.

The present invention provides resonant-cavity infrared photodetector (RCID) devices that include a thin absorber layer contained entirely within the resonant cavity.

In some embodiments of an RCID in accordance with the present invention, the absorber region is a single type-II InAs-GaSb interface situated between an n-type region comprising an AlSb/InAs n-type superlattice and a p-type AlSb/GaSb region.

In some embodiments, the absorber region comprises one or more quantum wells formed on an upper surface of the n-type region.

In some embodiments, the absorber region comprises a "W"-structured quantum well situated between two barrier layers, the "W"-structured quantum well comprising a hole quantum well sandwiched between two electron quantum wells.

In some embodiments, an RCID in accordance with the present invention includes a thin absorber region and an nBn or pBp active core within a resonant cavity.

In some embodiments, an RCID in accordance with the present invention is configured to detect light that propagates along the plane of the epitaxial structure rather than along its growth axis. Such an in-plane RCID structure can be used, for example, as the detection element of a compact on-chip chemical sensing package for sensing trace chemical species in a gas sample.

In some embodiments, an in-plane RCID can be part of a hybrid waveguide that includes a III-V RCID photodiode structure along with some other material within the waveguide, where the waveguide is used to input light propagating along the plane of the epitaxial structure into the RCID and to provide a waveguide for light propagating within the RCID.

In some embodiments, the p-region of the III-V RCID photodiode or pBp structure of the hybrid waveguide is ion-bombarded to suppress current flow within the bombarded regions. This may be beneficial, for example, in suppressing dark currents associated with surface leakage at the etched sidewalls of the patterned device.

DETAILED DESCRIPTION

Figure 1:
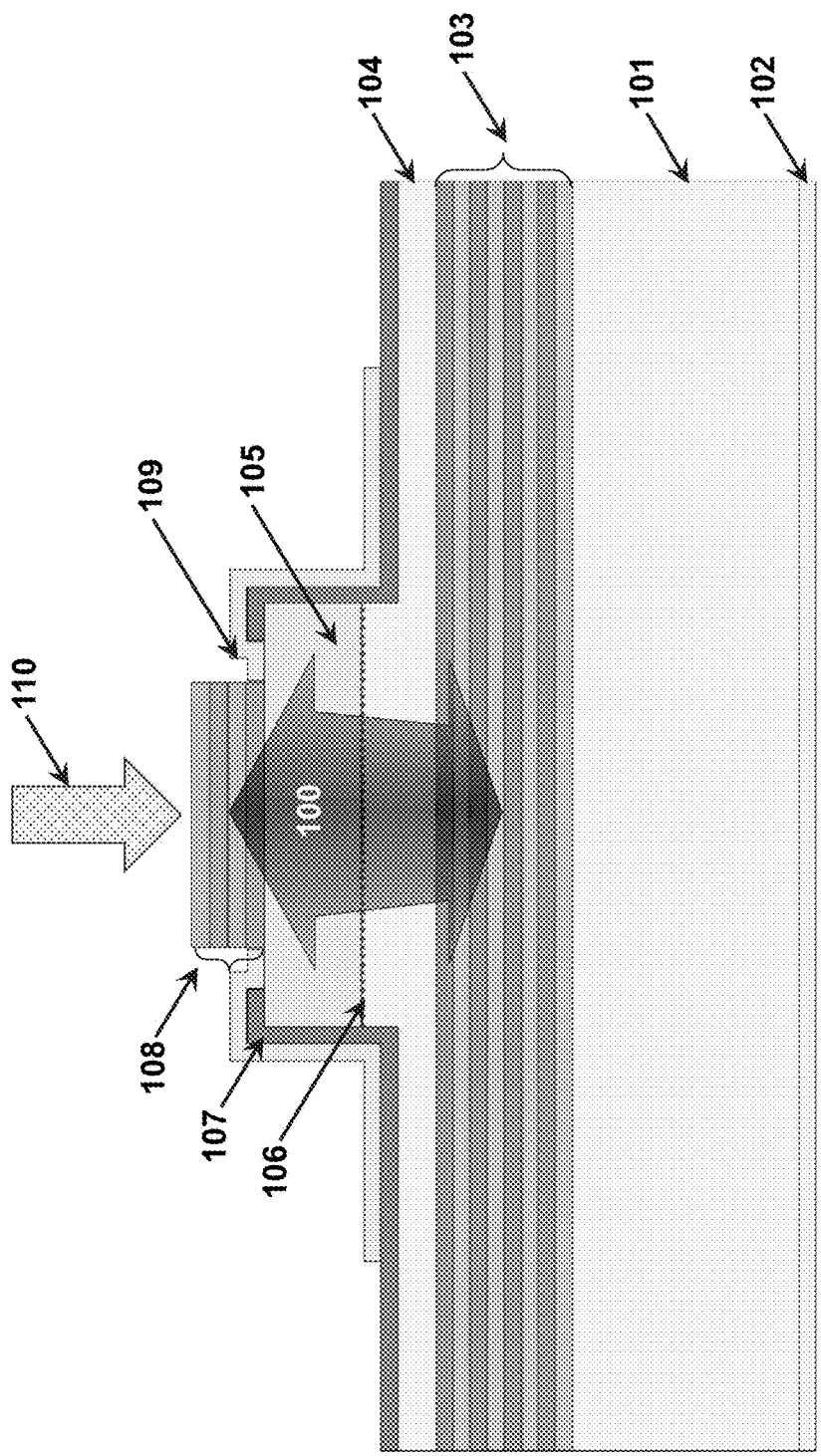
FIG. 1 is a block schematic depicting the epitaxial layering and mesa structure for an exemplary generic resonant cavity infrared detector (RCID) structure in accordance with the prior art.

The aspects and features of the present invention summarized above can be embodied in various forms. The following description shows, by way of illustration, combinations and configurations in which the aspects and features can be put into practice. It is understood that the described aspects, features, and/or embodiments are merely examples, and that one skilled in the art may utilize other aspects, features, and/or embodiments or make structural and functional modifications without departing from the scope of the present disclosure.

For example, the materials and the material layer thicknesses described herein are merely exemplary, and other materials and other material layer thicknesses may be employed as appropriate.

The following discussion assumes that the absorption of incident photons is dominated by interband processes that create an electron-hole pair. However, the extension to other processes such as intersubband absorption will be obvious to one skilled in the art.

In the absence of gain, quantum efficiency (QE) is limited to a maximum value of unity.

For a high QE to be realized, the thickness d of the absorbing layer of the photodetector must be comparable to or exceed $1/\alpha_0(\lambda)$, where $\alpha_0(\lambda)$ is the absorption coefficient, and either the minority-carrier diffusion length $L_D$ or the depletion width $W_d$ must be comparable to or greater than the absorber thickness. The latter condition assures that most of the electrons and holes generated by the optical signal are collected.

Typical absorption coefficients for the most common bulk, quantum well (QW), and superlattice (SL) III-V absorber materials that are sensitive in the short-wave infrared (SWIR) (2-3 µm), mid-wave infrared (MWIR) (3-5 µm), and long-wave infrared (LWIR) (8-14 µm) spectral regions range from about 1000 (for SLs in the LWIR) to 5000 cm$^{-1}$ in the SWIR. This implies that for a conventional interband IR detector structure to realize high QE, its absorber must be 2-10 µm thick. This is typically much greater than the width of the depletion region because of the presence of substantial background doping levels in narrow-gap materials.

We will first consider the example of a photodiode detector that collects minority carriers across a p-n junction. However it will be obvious to one skilled in the art that the principles discussed may easily be generalized to other geometries that do not contain p-n junctions, such as nBn or pBp majority-carrier-barrier structures, described below.

Since the usual absorber thickness of 2-10 µm in a conventional broadband IR detector significantly exceeds the typical depletion-layer thickness for a p-n junction, most or all of the absorber occupies the quasi-neutral region (on either the p or n side of the junction), in which the internal electric field is low. At low fields, the dominant fundamental dark transport mechanism is most often the current due to the diffusion of thermally generated carriers, although generation-recombination (G-R), parasitic tunneling, and surface leakage currents can also contribute significantly in non-ideal devices.

It is impossible to discriminate between the useful diffusion of photoexcited carriers (generated by the optical signal to be detected) and the competing diffusion of thermally excited carriers (noise). Consequently, the mechanism fundamentally limiting the minimum detectable signal is the diffusion dark current density at the operating bias. While the other parasitic processes mentioned above are not fundamental, they can contribute significantly for some design classes. In the limits of absorber thickness much shorter than the diffusion length ($L_D \alpha_0 \gg 1$) and the depletion width much narrower than the absorber thickness ($W_d \ll d$), the diffusion current is given by $$J_b \approx q d n_i^2 / (\tau_m N), \tag{6}$$

where q is the fundamental electron charge, d is the absorber thickness, $n_i \propto \exp(-E_g/2kT)$ is the intrinsic carrier density, $\tau_m$ is the minority-carrier lifetime, and N is the doping density. It follows that the dark current density increases strongly with rising temperature, and scales approximately linearly with the absorber thickness (up to the diffusion length). The resulting dependence of $J_b$ on T sets a limit on the maximum operating temperature for which the dark current noise is no greater than the optical background associated with blackbody radiation. The optical signal must compete with the dark current density and the optical blackbody background as the two fundamental noise sources that limit the minimum detectable signal.

It follows that within the limits specified above for which Eq. (6) is valid ($L_D \alpha_0 \gg 1$ and $W_d \ll d$), if the absorber can be thinned substantially, e.g., to a thickness d of 100 nm or less rather than several µm, the diffusion dark current at a given temperature would dramatically decrease. Moreover, the dark current will continue to decrease if the absorber thickness is decreased further such that the absorber becomes fully depleted, which occurs if its thickness becomes smaller than the depletion width ($W_d > d$). In that limit the dark current is typically limited by the generation-recombination (G-R) mechanism. When $W_d > d$ and the narrow-gap absorber is surrounded by wider-gap p and n regions, the G-R current density is given by $$J_b \approx q d n_i / \tau_c, \tag{7}$$

where $\tau_c$ is the carrier lifetime within the depletion region. Because the depletion region is defined by a relatively high internal electric field, the carrier lifetime in that environment may be somewhat shorter than the minority-carrier lifetime $\tau_m$ in an n or p region with the same bandgap. As in the more conventional case of Eq. (6) above, in the fully-depleted limit of Eq. (7) the dark current density again increases strongly with rising temperature, and scales approximately linearly with the absorber thickness. And again, the resulting dependence of $J_b$ on T sets a limit on the maximum operating temperature for which the dark current noise is no greater than the optical background associated with blackbody radiation.

While it is apparent from Eqs. (6) and (7) for different limits of the absorber thickness relative to the depletion width that significantly thinning the absorber can substantially reduce the dark current, in a conventional photodetector architecture this would be disadvantageous because most of the signal photons would pass through the absorber without being absorbed, and hence QE≪1.

It has been demonstrated in the prior art that this degradation of QE can be avoided by placing the absorber within a vertical resonant cavity, which significantly enhances the absorption per unit length for wavelengths near the cavity resonance. This strategy has been implemented successfully at telecommunication wavelengths (λ=1.3-1.6 µm), where the primary motivation is usually to increase the detector speed by reducing the absorber thickness across which the photogenerated minority carriers must diffuse. See M. Selim Ünlü et al., "Resonant Cavity Enhanced Photonic Devices," J. Appl. Phys. 78, 607 (1995). While those devices benefit from the general advantages of the resonant cavity architecture as known to the prior art, no previous reports have discussed, proposed, or implemented full carrier depletion or the other defining features of the designs comprising the present invention.

In many infrared detection applications, such as focal plane arrays for IR imaging, the objective is to maximize the sensitivity to input signals spanning a broad spectral bandwidth such as the entire SWIR, MWIR, or LWIR band. In such applications, the resonant cavity approach is disadvantageous, since the detectivity is enhanced only within a narrow spectral window corresponding to the cavity resonance, whereas the net broadband signal is reduced. On the other hand, the resonant cavity approach may be quite beneficial in other applications that require sensitivity to only a narrow range of wavelengths, such as to detect a laser signal or in hyperspectral detection. In those applications, a broadband response is actually disadvantageous because any sensitivity to wavelengths outside the narrow spectral band of interest represents optical background noise.

In the present disclosure, we will assume that the optical signal is incident from the "top," i.e., from above the epitaxial detector structure that is grown "on top of" a substrate. However, generalization to the alternative case where the signal is incident from the "bottom," i.e., the substrate side (with the substrate intact in some embodiments or removed in others), will be obvious to one skilled in the art.

As noted above, some resonant-cavity absorption enhancement at wavelengths beyond 2.5 μm may, in fact, be achievable using conventional III-V bulk (e.g., InAs and InAsSb) or superlattice (e.g., InAs—Ga(In)Sb and InAs—InAsSb) absorbers in p-n junction or barrier (nBn and pBp) configurations from the prior art. See Martyniuk et al., supra.

However, no previous reports for either conventional or resonant-cavity IR detectors have proposed or implemented the defining features of the designs comprising the present invention, which employs configurations that would be either unfeasible or disadvantageous in a conventional broadband IR detector.

Even though the diffusion current density that typically controls the dark current of absorbers that are much thicker than the depletion width (see Eq. (6) above) can be suppressed by moderate doping of the absorber, the carrier lifetimes relevant to the fully-depleted and non-fully-depleted cases are not necessarily the same. In some embodiments of the invention, the lifetime is controlled by Auger recombination, which is strongly suppressed by depleting the absorber region of both electrons and holes as compared to a quasi-neutral absorber (see Eq. (7) above).

Because the minority-carrier lifetime $\tau_m$ in a conventional non-depleted IR material with high intrinsic carrier density tends to be limited by the Auger process, whose rate scales approximately as the cube of the carrier density, $\tau_c$ in the depletion region can exceed $\tau_m$ by orders of magnitude if most of the extrinsic and intrinsic electrons and holes can be depleted from the absorber. Furthermore, since the dark-current density of Eq. (7) is proportional to $n_i$ rather than $n_i^2$ for the diffusion current of Eq. (6), the increase of $J_b$ with operating temperature becomes much more gradual. These considerations hold if the detector is a photodiode in which the absorber region is surrounded by n-type and p-type regions with significantly larger energy gaps than the absorber. See I. Vurgaftman, E. H. Aifer, C. L. Canedy, J. G. Tischler, J. R. Meyer, J. H. Warner, E. M. Jackson, G. Hildebrandt, and G. J. Sullivan, "Graded band gap for dark-current suppression in long-wave infrared W-structured type-II superlattice photodiodes," *Appl. Phys. Lett.* 89, 121114 (2006); and C. L. Canedy, E. H. Aifer, J. H. Warner, I. Vurgaftman, E. M. Jackson, J. G. Tischler, S. P. Powell, K. Olver, J. R. Meyer, and W. E. Tennant, "Controlling dark current in type-II superlattice photodiodes," *Infrared Phys. Technol.* 52, 326 (2009). In such a photodiode, thermal generation in the n- and p-type regions become negligible because they scale as $\exp(-E_g/kT)$.

Configurations that allow the absorber of an IR photodiode to be placed entirely within the depletion region of the p-n junction at low bias have not been discussed previously. To maintain high QE, the absorber in a conventional broadband IR detector (such as the structure discussed in Vurgaftman et al., supra) must be several microns thick, which is far greater than any depletion width induced by realistic p- and n-type doping levels. While it is possible in principle to fully deplete the thick absorber region of a conventional photodiode (see D. Lee, M. Carmody, E. Piquette, P. Dreiske, A. Chen, A. Yulius, D. Edwall, S. Bhargava, M. Zandian, and W. E. Tennant, "High-operating temperature HgCdTe: A vision for the near future," *J. Electronic Materials* 45, 4587 (2016)), it is generally impractical since it requires unrealistically low doping levels and/or the application of a very high bias with voltage scaling as $d^2$.

On the other hand, the absorber of the present invention is inserted entirely into the depletion region, which is possible even at zero bias because the RCID enhancement allows the absorber to be very thin (≤100 nm, and in many embodiments as thin as 10 nm) while retaining high QE. This will substantially suppress Auger recombination and its inverse process, impact ionization. For most III-V IR detector materials, Auger processes dominate the dark current at higher operating temperatures. The substantial suppression of Auger recombination up to temperatures approaching ambient will be a significant advantage in practical systems for chemical sensing and other applications, since it will become possible to reach background-limited sensitivity at a temperature that does not require cryogenic cooling.

In some embodiments, various barriers or transition superlattices may also be inserted between the absorber and the main portions of the n- and p-regions. Alternatively, the doping level in any region may be varied as a function of position. Such variants may serve to minimize thermal generation, fine-tune the band alignments, and/or aid carrier transport between the absorber and the n- and p-regions.

Figure 2:
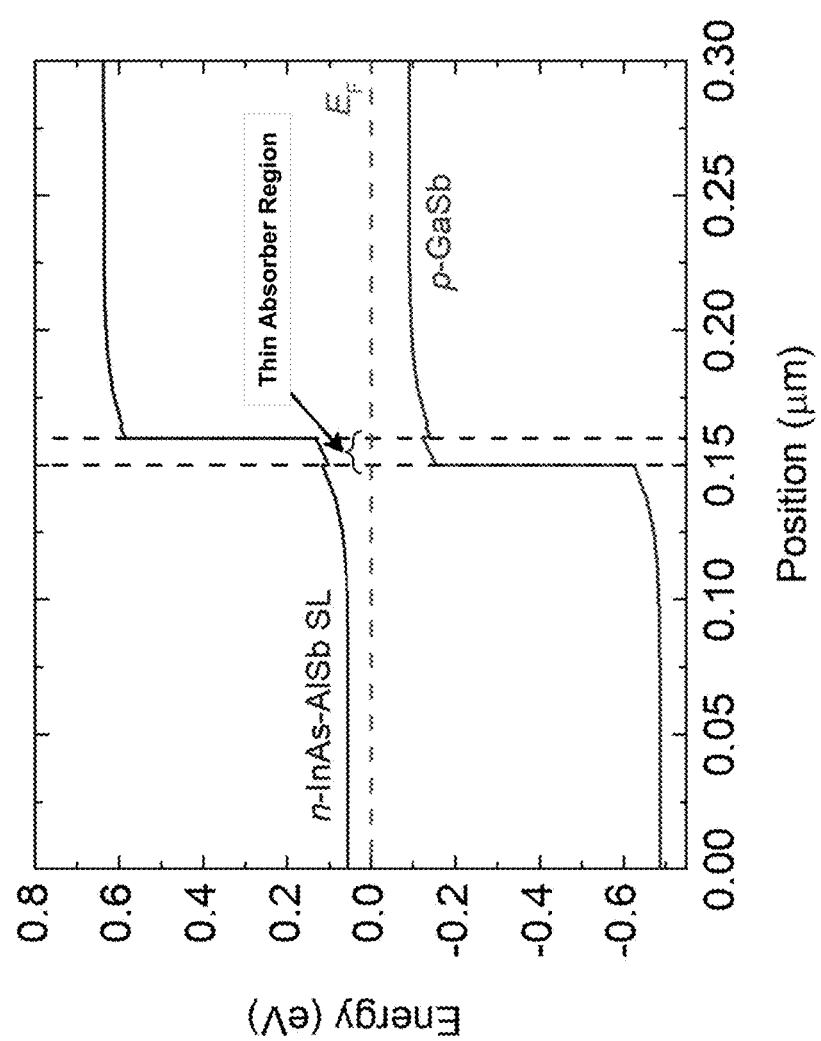
FIG. 2 is a plot depicting the conduction band minimum and valence band maximum energy levels, along with the Fermi level energy, for an exemplary RCID having a thin absorber region incorporated into a p-n junction in accordance with the present invention.

FIG. 2 schematically illustrates the spatial profiles for the conduction-band minimum and valence-band maximum energy levels (solid), along with the Fermi level (dashed) for an exemplary resonant-cavity detector having a 10-nm-thick thin absorber surrounded by n- and p-regions in accordance with the present invention. It will be noted that in this as in all other band diagrams in the FIGURES of the present application, the spatial dimensions of the FIGURE are not drawn to scale.

In the exemplary embodiment of FIG. 2, the doping levels in the n- and p-type regions are both $10^{17}$ cm$^{-3}$, although a range of doping levels may be employed on either side of the junction. In this embodiment, the absorber is assumed to be undoped, although the carriers generated by typical unintentional doping levels (e.g., ≤$10^{16}$ cm$^{-3}$) will be swept away by the internal field.

It is apparent from FIG. 2 that the internal electric fields represented by the band curvatures will deplete the absorber of electrons and holes by sweeping them into the adjacent n- and p-regions, respectively. The internal field will also at least partly deplete the intrinsic carriers of both types, whose densities vary strongly with the temperature of operation. Thus for quasi-thermal-equilibrium, far fewer carriers will be present in this thin absorber than the normal intrinsic population present in the much thicker absorber of a broadband detector. This depletion of the carrier population will substantially suppress the Auger contribution to the dark current, as discussed above.

However, if the absorber has a net p-type doping and the depletion of majority holes is incomplete, in accordance with the invention it may be advantageous to design the structure such that the conduction-band minimum in the absorber is more nearly aligned with the conduction band in the n-region (at left in the figure). This adjustment will serve to make it more energetically favorable for majority holes in the absorber to deplete into the p-region that now has a larger offset. Consequently, Auger recombination will be strongly suppressed because very few carriers of either type remain in the absorber at zero bias.

Conversely, if the absorber has a net n-type doping and the majority electrons do not fully deplete, in accordance with the invention it is advantageous to design the structure such that the valence band in the absorber is more nearly aligned with the valence band in the p-region (at right in the figure).

In a third case, if the population of intrinsic electrons and holes exceeds the extrinsic doping level at the temperature of operation, in accordance with the invention the bands in the various regions of the structure should be aligned such that the conduction-band minimum is aligned or somewhat higher in the active region than in the n-region and the valence band maximum is aligned or somewhat lower in the active region than in the p-region, so that both electrons and holes tend to flow out of the active region and deplete it at zero bias. This is the case illustrated in FIG. 2.

Some fine tuning of the band alignments may be required to achieve the maximum suppression of Auger recombination, which will also depend on the relative Auger coefficients for processes involving two electrons and one hole ($\gamma_3^{nnp}$) as compared to those that involve two holes and one electron ($\gamma_3^{ppn}$). If $\gamma_3^{ppn} > \gamma_3^{nnp}$, for example, hole extraction from the active region has a greater effect on the Auger recombination rate than electron extraction.

For both types of net doping in the absorber, in accordance with the invention if the absorber is not fully depleted at zero bias, the application of a reverse bias may complete the depletion of electrons and holes to assure that Auger recombination is suppressed. Generally, the required bias will be relatively small because the region to be depleted is quite thin.

Besides providing the potential for substantially suppressing Auger recombination, the extreme thinness of the RCID absorber in accordance with the present invention considerably broadens the design space to include options that are unavailable to detectors with conventional thick absorbers.

The most extreme example is an absorber consisting of a single type-II interface occupying the boundary between the n- and p-type regions of the diode.

Figure 3:
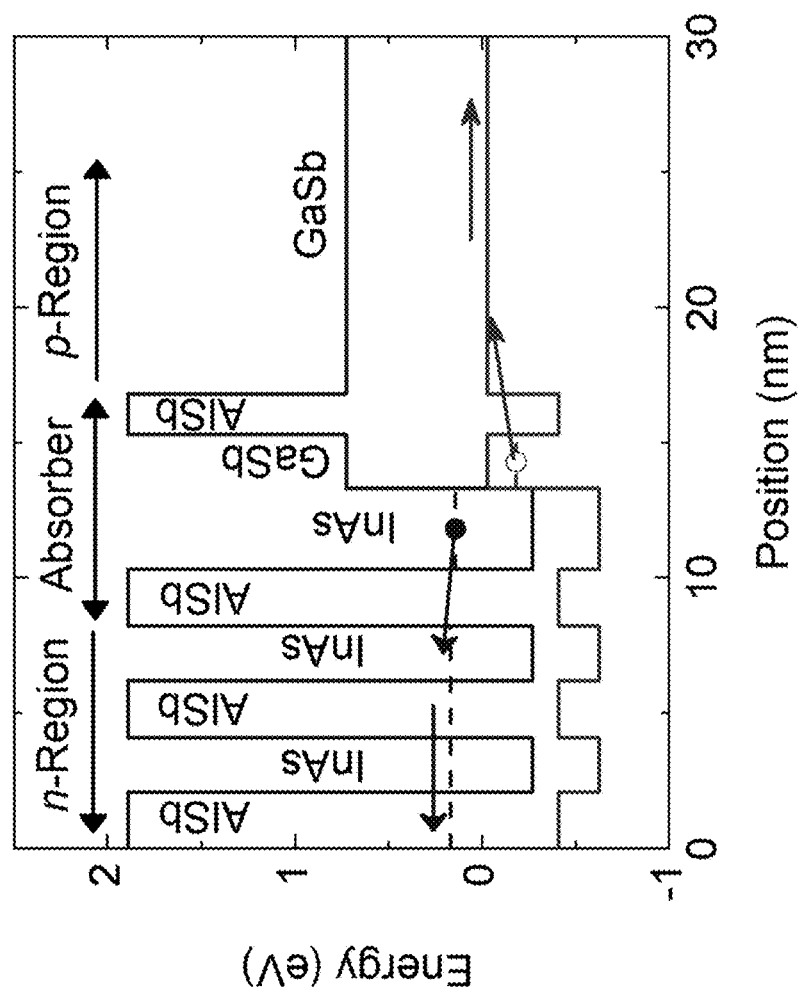
FIG. 3 is a plot illustrating, on an expanded scale, the energy band profiles and electron and hole ground state subband energy levels for an exemplary absorber, n region, and p region of an RCID structure of the type illustrated in FIG. 2.

FIG. 3 illustrates the energy band structure of an exemplary embodiment of such an RCID in accordance with the present invention, where the absorber region consists of a single type-II InAs—GaSb interface, where the active InAs layer has a thickness of 30 Å and the active GaSb layer has a thickness of 20 Å.

In the exemplary embodiment illustrated in FIG. 3, the n-region is an InAs-AlSb superlattice that is strain-compensated to match the lattice constant of the GaSb substrate. The InAs layers in the superlattice are slightly thinner than the active InAs QW of the absorber. This relationship serves to place the lowest SL miniband at a slightly higher energy than the lowest conduction subband of the active QW. The active hole QW is a single GaSb layer bounded by an AlSb barrier whose highest valence subband lies somewhat lower in energy than the valence band maximum of the p-region.

The p-region in this exemplary embodiment is p-GaSb. Again, other bulk or superlattice materials may be substituted so long as the band alignments approximate the optimal conditions discussed above and the p-region conduction-band minimum is much higher than the absorber conduction band.

The total absorber thickness in this exemplary structure is 8 nm, counting the AlSb barriers on each side of the active InAs and GaSb layers. The active optical transitions in this structure are between valence states having wavefunctions concentrated mostly in the active GaSb QW and electron states with wavefunctions concentrated mostly in the active InAs QW.

Assuming operation at 300 K, the energy gap for a diode having a structure as shown in FIG. 3, with an absorber thickness of 8 nm, is 320 meV ($\lambda_{co}$=3.8 μm). For a resonance wavelength of $\lambda_{res}$=3.4 μm, the calculated absorption per pass (A) is 0.17%. With $R_2 \approx 100\%$, a top mirror reflectivity of $R_1$=97.5% then yields QE≈80% and δλ≈4 nm.

Besides strongly suppressing the dark current associated with Auger recombination by depleting electrons and holes from the absorber, an important advantage of a structure in accordance with the embodiment illustrated in FIG. 3 is that it provides the potential to absolutely minimize thermal generation noise. Since thermal generation in the n- and p-type regions is negligible due to their very large energy gaps, the only place in the entire detector structure where the presence of defects can induce dark current associated with Shockley-Read recombination is in the immediate vicinity of the single narrow-gap InAs-GaSb interface (as determined by the overlap of the electron and hole wavefunctions). As long as this interface region is of high quality, the dark current for a given cut-off wavelength and temperature may be suppressed to an unprecedented level.

A possible disadvantage of a structure in accordance with this embodiment is that the absorption at the single interface is relatively weak because there is limited overlap of the relevant electron and hole wavefunctions residing mostly in the active InAs and GaSb QWs, respectively. Nevertheless, as described above the simulated absorption per pass of 0.17% is sufficient to provide a high QE using a realistic top mirror reflectivity. In other words, the resonant cavity enhances the useful photogeneration, but not the deleterious thermal generation.

A further advantage of this embodiment of the invention, as well as many of the others discussed below, over the thick absorbers employed in the prior art is that the absorber need not be carefully strain-compensated or lattice-matched to the GaSb (or some other such as InAs) substrate to avoid dislocations that can short the device or otherwise degrade its performance. It is only important to assure that the absorber thickness not exceed the critical value for dislocation-free growth associated with its particular design.

Numerous variations on the embodiment illustrated by the band diagram shown in FIG. 3, in which the RCID absorber consists of a single interface, will be obvious to one skilled in the art.

For example, the energy gap (and cut-off wavelength) can be easily varied by adjusting the thickness of the active InAs QW, so as to increase or decrease the quantum confinement energy. In other cases, in order to minimize the dark current, it may be advantageous to design the cut-off wavelength for the absorber to be just close enough to the resonance wavelength of the cavity so that the needed value of absorption per pass can be achieved. In other cases it may be straightforward to replace the InAs—AlSb n-type superlattice with InAs—AlInSb, InAsSb—AlSb or one of many other variations. Alternatively, a bulk material such as InGaAsSb may be employed. The active InAs layer may be replaced by a ternary alloy such as InAsSb or a quaternary alloy such as InGaAsSb. In other embodiments, as discussed above, the structure may be redesigned for optimal performance in the cases of net n-type doping of the active region or when the intrinsic carrier population exceeds the extrinsic doping level at the operating temperature of interest.

On the p-side of the single-interface absorber of FIG. 3, alternative configurations may eliminate the GaSb QW or replace it with GaInSb, GaAlSb, or some other related alloy. The barrier compositions and thickness may also be varied, and transition superlattices may be incorporated on one or both sides of the absorber to control the wavefunction profiles, band alignments, carrier transport, and distribution of the quasi-equilibrium carrier populations. In addition, as discussed below, when Shockley-Read rather than Auger recombination dominates the diffusion current, it may be advantageous to position the single-interface absorber in a quasi-neutral region of a p-n junction or an nBn structure, rather than within the depletion region of the junction.

As discussed below, if the absorber has a net p-type doping concentration that exceeds the intrinsic carrier concentration, the conduction-band minimum in the n-region should roughly align with the conduction-band minimum in the absorber (the case shown in FIG. 3).

On the other hand, if the absorber has a net n-type doping that exceeds the intrinsic concentration, the conduction-band minimum in the n-region should be somewhat lower than that in the absorber so as to make it more energetically favorable for majority electrons in the absorber to deplete into the n-region at zero bias.

In both cases the n-region conduction band should be low enough to allow the efficient collection of photoexcited electrons, but not so low that excessive thermal generation is induced between n-region electron states and absorber hole states.

Numerous variants involving other n-type SL constituents such as InAs-AlInSb, or a lattice-matched quaternary alloy such as InGaAsSb or InAlAsSb, may also be used to form the n-region as long as its conduction band is optimally aligned as discussed above and its valence band is much lower than the absorber valence band.

For example, in accordance with the invention, the alignment shown for the embodiment illustrated in FIG. 3 is optimal when the net doping of the absorber is p-type and exceeds the intrinsic carrier concentration at the device operating temperature. On the other hand, if the net doping of the absorber is n-type and exceeds the intrinsic concentration, the valence-band maxima in the absorber and p-region should roughly align. In the third case, in which the intrinsic carrier concentration exceeds the extrinsic doping level in the active region, the alignment of the valence band maximum in the p-region relative to that in the absorber should lie somewhere between the other two limit Other embodiments of the invention employ ultra-thin absorbers consisting of one or a few type-I or type-II QWs rather than the single interface of FIG. 3.

Figure 4:
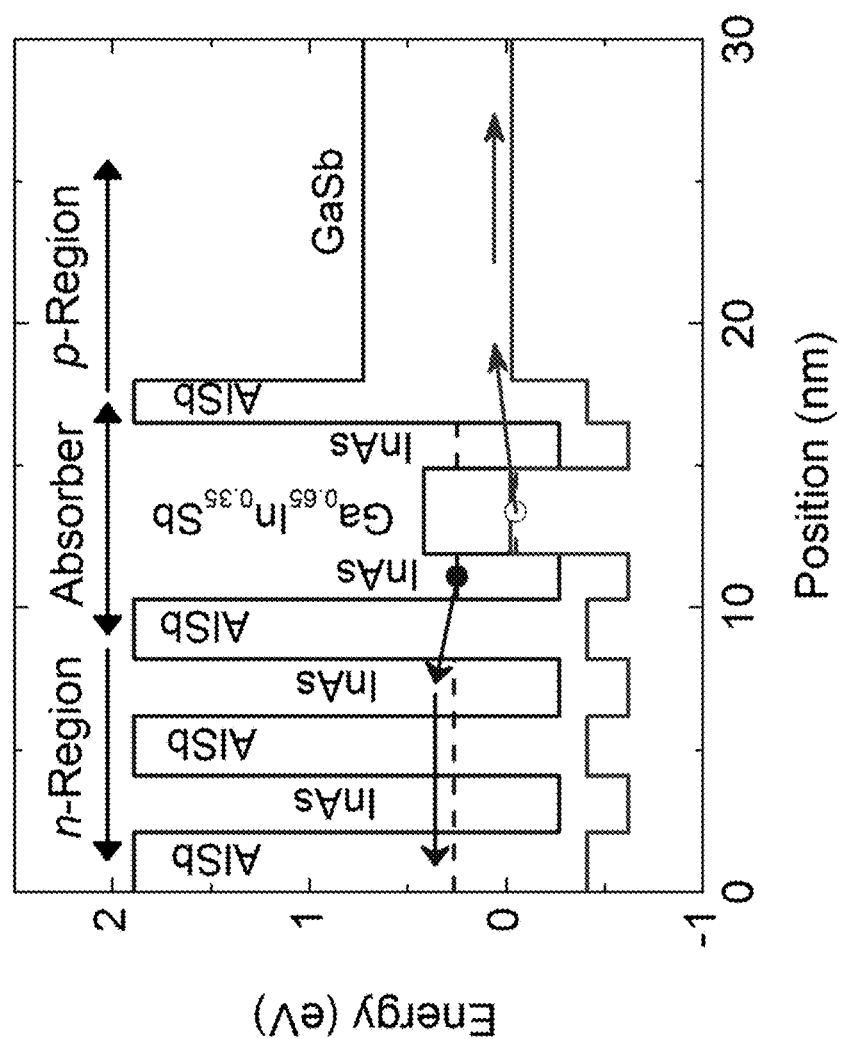
FIG. 4 is a plot illustrating energy band profiles and energy levels for another exemplary embodiment of a RCID having a thin absorber, n region, and p region in accordance with the present invention.

The band diagram in FIG. 4 illustrates aspects of an exemplary embodiment of an RCID incorporating such an absorber, where the absorber is in the form of a single type-II InAs/Ga(In)Sb/InAs "W"-structured multiple QW heterostructure comprising an InAs electron QW, a GaInSb hole QW, and InAs electron QW, with the W-structured QW being sandwiched between two AlSb barriers on either side. See J. R. Meyer et al., "Type-II quantum-well lasers for the mid-wavelength infrared," *Appl. Phys. Lett.* 67 (6), pp. 757-759 (1995); and E. H. Aifer et al., "W-structured type-II superlattice long-wave infrared photodiodes with high quantum efficiency," *Appl. Phys. Lett.* 89, 053519 (2006)); see also U.S. Pat. No. 5,793,787, to Meyer et al., entitled "Type II Quantum Well Laser with Enhanced Optical Matrix" (1998). As in FIG. 3, the band bending associated with charge transfer between the different layers and regions is not shown.

Thus, in the exemplary embodiment of such a structure illustrated in FIG. 4, the absorber is a single type-II "W"-structured QW consisting of a 16 Å InAs electron quantum well, a 30 Å GaSb hole quantum well, and a second 16 Å InAs electron QW, with the absorber having a net thickness of less than 10 nm and an energy gap of 300 meV ($\lambda_{co}$=4.2 µm) at 300 K. For a resonance wavelength of 3.4 µm, an absorption per pass of 0.34% was calculated, which doubles that of the single-interface structure shown in FIG. 3 due to enhancement of the wavefunction overlap. With $R_2 \approx 100\%$, simulations by the inventors yielded that a top mirror reflectivity of $R_1$=95% will provide QE≈80%, with and $\delta\lambda \approx 11$ nm.

By positioning the central Ga(In)Sb hole QW between two InAs electron QWs, the "W" configuration provides greater overlap of the electron and hole wavefunctions than the type-II single-interface structure of FIG. 3, which in turn increases the absorbance per pass. If additional QWs are added, high QE can be obtained with a lower top mirror reflectivity. The FWHM of the resonance would also broaden correspondingly.

As with the previous structure illustrated in FIG. 3, in accordance with the present invention, if the net doping in the absorber is p-type and exceeds the intrinsic carrier population the conduction band on the n-type side of the active absorber should approximately align with the lowest electron subband in the type-II "W" QW, while the valence band maximum on the p-type side should be slightly higher than the topmost hole subband in the active QW(s). This is the configuration shown in FIG. 4. In accordance with the present invention, the optimal alignments can be altered as discussed above in the alternative cases where the net doping of the active region is n-type and larger than the intrinsic carrier population, or when the intrinsic carrier density exceeds the extrinsic doping level. The use of wide-gap materials in the n- and p-regions again minimizes thermal generation everywhere except within the absorber.

Numerous other variations are possible.

For example, the cut-off wavelength for the active "W" QW can be easily tuned by adjusting the thicknesses of the InAs QWs. In addition, the two InAs QWs need not have the same thicknesses, or the single or multiple type-II "W" QWs may be formed from InAs—InAsSb or InAs—InAsSb—InAs ("Ga-free") layering. Alternatively, if multiple QWs are employed, it may be advantageous to form a superlattice such as InAs—Ga(In)Sb or InAs-InAsSb, rather than multiple "W" QWs separated by AlSb barriers. In other embodiments, the one or more QWs in the absorber may be constructed using a type-I or type-II configuration that does not form a "W" structure. Numerous variations on the active material constituents may also be employed, such as InAsSb or InGaAs electron QWs, Ga(Al)Sb or GaAsSb hole QWs, and AlGaSb or AlAsSb barriers. As discussed above, additional barriers or transition superlattices may also be added on one or both sides of the active absorber QWs.

Figure 5:
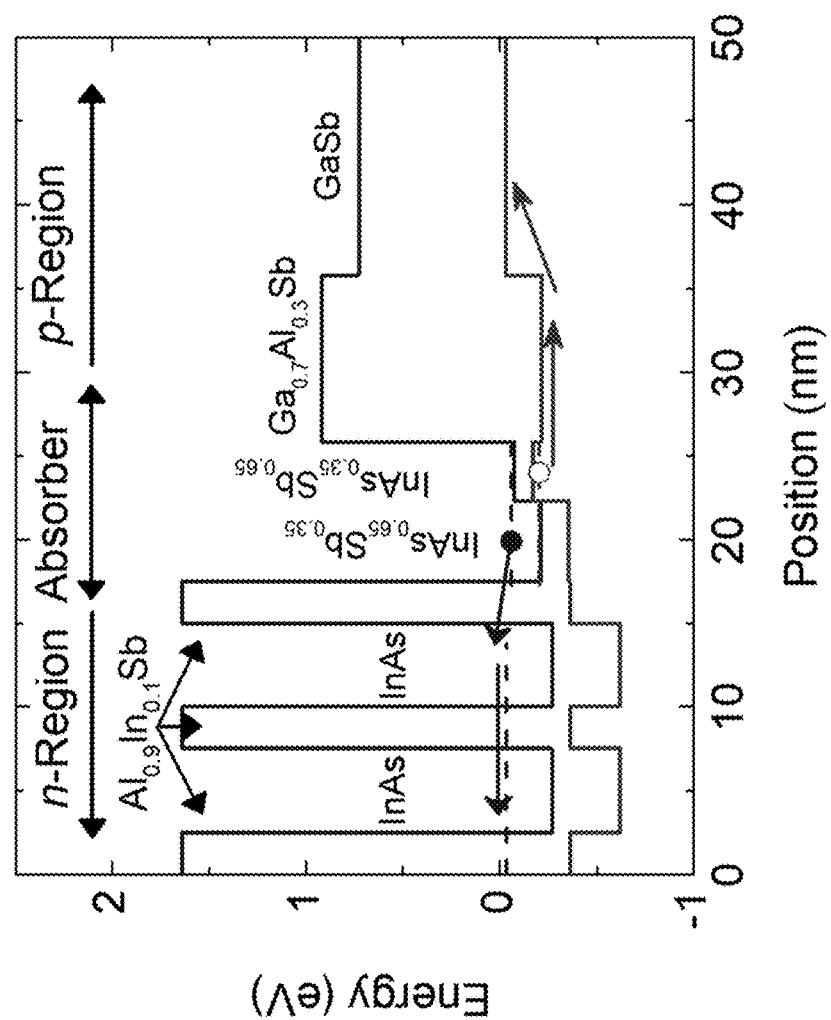
FIG. 5 is a plot illustrating energy band profiles and energy levels for another exemplary embodiment of a thin absorber, n region, and p region for an RCID in accordance with the present invention.

The band diagram in FIG. 5 illustrates aspects of another exemplary embodiment of an RCID device in accordance with the present invention which includes an ultra-thin LWIR absorber consisting of a single type-II $InAs_{0.65}Sb_{0.35}$ (48 Å)-$InAs_{0.35}Sb_{0.65}$(35 Å) QW. In the embodiment illustrated in FIG. 5, the net absorber thickness d is less than 11 nm, and its energy gap is 130 meV ($\lambda_{co}$=9.3 µm) at 150 K, though, as noted above, one skilled in the art will understand that other materials and material layer thicknesses may be employed as appropriate. Again, the band bending associated with charge transfer between the different layers is not shown in FIG. 5.

In the embodiment illustrated in FIG. 5, the absorber is bounded on one side by a strain-balanced n-type InAs(50 Å)-$Al_{0.9}In_{0.1}Sb$(25 Å) superlattice whose alignment provides efficient extraction of the photo-generated electrons. In order to approximately align the valence-band edge of the absorber QW with the valence-band edge of the p-region, we may employ p-$Al_{0.45}Ga_{0.55}As_{0.04}Sb_{0.96}$, which is lattice-matched to the GaSb substrate, or $Al_{0.45}Ga_{0.55}Sb$ as in the figure, which is not lattice matched but with small enough strain that a thin layer is unlikely to introduce dislocations.

As discussed above for other exemplary embodiments, in accordance with the present invention, if the net doping in the absorber is p-type and larger than the intrinsic carrier density, the conduction band minimum on the n-type side of the absorber should approximately align with the ground state electron subband in the type-II Ga-free QW, while the valence-band maximum on the p-type side should be slightly higher than the topmost hole subband in the active QW(s). This is the configuration shown in FIG. 5. However, the optimal alignments can be altered as discussed above in the alternative cases where the net doping of the active region is n-type and larger than the intrinsic carrier population, or when the intrinsic carrier density exceeds the extrinsic doping level.

Also in the embodiment illustrated in FIG. 5, the absorber is bounded on the other side by a p-GaSb layer separated from the absorber by a $Ga_{0.55}Al_{0.45}Sb$ barrier layer having a nominal thickness of 10 nm. The role of the barrier layer is to prevent excessive thermal generation at what would otherwise be a very narrow bandgap or semimetallic interface between the InAsSb/InAsSb QW absorber and the GaSb p-region; however, in some other embodiments, the barrier layer can be omitted such that the p-GaSb layer is directly adjacent the QW absorber. While some absorption may occur at the interface between the InAsSb/InAsSb QW absorber and the GaAlSb layer of the structure in FIG. 5 (or the p-GaSb in an embodiment without the barrier), that will simply contribute additional absorption at roughly the same band edge as the QW.

At an operating temperature of 150 K, the QW energy gap is 130 meV ($\lambda_{co}$=9.3 μm). For a resonance wavelength of 9.2 μm, simulations by the inventors projected an absorption per pass of A=0.18%. With $R_2 \approx 100\%$, projections yielded that a top mirror reflectivity of $R_1$=95% will provide QE≈80% with δλ≈23 nm. While the assumed operating temperature of 150 K is much higher than for a conventional broadband LWIR detector with background-limited detectivity D*, the invention's strong suppression of dark currents will help make it feasible.

It should be noted that the exemplary embodiment illustrated in FIG. 5 relies on the combination of two $InAs_{1-x}Sb_x$ alloy compositions that cannot be strain-balanced or lattice-matched to any binary substrate that is commonly used in existing state-of-the-art IR detectors to provide high-quality growth. Therefore, thick absorber regions employing this design would generate dislocations that seriously compromise the device performance.

In addition, although the $InAs_{1-x}Sb_x$ alloy system offers an attractive range of bandgaps and is known to display a long minority-carrier lifetime when grown with high material quality, its use in conventional broadband IR detectors is severely limited by strain considerations. Since only one particular alloy composition, x≈0.08, has a lattice constant matching that of a GaSb substrate (and only the binary endpoints match the lattice constants of InAs and InSb substrates), access to other alloy compositions, and, therefore, to other cut-off wavelengths, requires the employment of either metamorphic growth on a lattice-mismatched substrate or some form of strain compensation to GaSb or another binary substrate. While metamorphic growth methods have made progress in recent years, see D. Wang et al., "Metamorphic InAsSb-based barrier photodetectors for the long wave infrared region," *Appl. Phys. Lett.* 103, 051120 (2013), the material quality still falls far short of that attainable using strain-compensated or lattice-matched growth.

Strain compensation has been used to match superlattices such as $InAs/InAs_{1-x}Sb_x$ to the GaSb substrate lattice constant. See J. Lu et al., "Evaluation of antimony segregation in $InAs/InAs_{1-x}Sb_x$ type-II superlattices grown by molecular beam epitaxy," *J. Appl. Phys.* 119, 095702 (2016). However, the range of InAsSb alloy compositions and layer thicknesses that may be employed with acceptable strain is substantially limited. The extraction of holes from a thick n-type InAs-InAsSb superlattices with a short minority-carrier diffusion length is also an issue that can limit the QE, especially at longer cutoff wavelengths. A significant advantage of the invention is that its ultra-thin absorber (≤100 nm) provides very efficient minority-carrier extraction even when the minority-carrier diffusion length is relatively short.

Many other InAsSb—InAsSb or InAs—InAsSb QW layer combinations may be employed as variations on the embodiment illustrated in FIG. 5. These are capable of spanning any desired MWIR to LWIR cut-off wavelength, although the n-type and p-type regions on opposite sides of the absorber must be modified to provide appropriate alignment of the conduction and valence band energies.

A single-layer $InAs_{1-x}Sb_x$ QW or slightly thicker bulk-like InAsSb alloy of any composition may also be employed, as long as the absorber thickness does not exceed the critical thickness for growth without dislocations. For example, a cut-off wavelength of 5.0 μm can be obtained using a structure somewhat similar to that in FIG. 5, with an absorber consisting of a 100-Å-thick $InAs_{0.35}Sb_{0.65}$ QW (rather than the InAsSb/InAsSb QW shown in FIG. 5), bounded on the left by an InAs(34 Å)-AlSb(35 Å) n-type region and on the right by the same $Ga_{0.7}Al_{0.3}Sb$ barrier (or a GaAlAsSb barrier) and the same GaSb p-layer as in the embodiment shown in FIG. 5. As discussed above, to ensure the optimal suppression of Auger recombination as a result of depleting majority and intrinsic carriers from the active region, the band alignments on the n- and p-sides of the active region may require adjustments based on whether the net doping concentration in the active region is n-type or p-type, whether it is larger or smaller than the intrinsic carrier concentration, and whether $\gamma_3^{ppn}$ or $\gamma_3^{nnp}$ is larger.

For all of the embodiments falling under the scope of the invention, if the band alignments are insufficient to sweep most of the extrinsic and intrinsic carriers out of the active region at zero bias, the application of a reverse bias may serve to more fully deplete the active region of the device.

It was mentioned above that placing the absorber entirely within the depletion region may be advantageous at higher operating temperatures, since sweep-out of the intrinsic and extrinsic carriers will reduce the dark current associated with Auger recombination due to the intrinsic carrier populations. On the other hand, at lower temperatures and longer wavelengths, full depletion may be undesirable if defect-assisted rather than Auger processes dominate the dark current, as they do in state-of-the-art III-V MWIR and LWIR detectors. A detector in accordance with the present invention can be designed so as to place the absorber either entirely within the depletion region when Auger processes dominate, or in a quasi-neutral region with much lower electric field when defect processes dominate; which of these options is preferable will depend on the absorber material choice, the spectral band, and the temperature of operation.

To further enhance the device functionality, other embodiments of an RCID device in accordance with the present invention can include an absorber region formed by one or more asymmetric QWs, e.g., InAs/GaInSb. When a variable electric field (controlled by the bias voltage) is applied to this type of asymmetric structure, the opposite shifts of the electron and hole wavefunctions in their respective QWs induce a red or blue shift of the band edge. This provides a mechanism for dynamically tuning between strong resonance-enhanced absorption for one operating bias, vs. minimal absorption of the resonance wavelength at another bias for which the cut-off wavelength is shifted beyond the cavity resonance. A red shift of the absorption edge by the application of an electric field can also be employed in type-I quantum wells.

Other embodiments of an RCID in accordance with the present invention employ variations on nBn or pBp configurations rather than a p-n junction. See S. Maimon et al., "nBn detector, an infrared detector with reduced dark current and higher operating temperature," *Appl. Phys. Lett.* 89, 151109 (2006); A. Soibel et al., "Room temperature performance of mid-wavelength infrared InAsSb nBn detectors," *IR Phys. Technol.* 70, 121 (2015); and E. A. Plis et al., "Bias Switchable Dual-Band InAs/GaSb Superlattice Detector With pBp Architecture," *IEEE Phot. J.* 3, 234 (2011).

In conventional nBn or pBp detectors, the absorber is thick and placed on one side of the electron (for nBn) or hole (for pBp) barrier. In nBn or pBp embodiments of an RCID in accordance with the present invention, the absorber will be much thinner and is placed within the resonant cavity formed by the top and bottom dielectric and/or grown semiconductor mirrors, the first n-type (or p-type) region, the electron or hole barrier region, and the second n-type (or p-type) region, with the absorber being surrounded on both sides by wider-gap layers to reduce the unwanted thermal generation.

In the case of the nBn or pBp embodiments of an RCID in accordance with the present invention, the band edge for minority carriers in the barrier does not need to be precisely aligned with that of the absorber. The band discontinuity that has to be present in either the conduction or valence band will manifest as an increased operating bias, which can be relatively small for the required energy-gap difference of 5-10 $k_B T$.

The thin absorber can also be placed near an antinode of the resonant cavity, and as with all of the structures discussed above, the detectivity of an RCID in accordance with the nBn or pBp embodiments of the present invention will benefit from the substantial suppression of the dark current originating in the thin absorber region.

For a conventional device with a thick absorber, the nBn geometry typically induces a smaller internal electric field within or at the boundaries of the absorber, since if properly designed, there is no depletion region associated with the presence of a p-n junction. The avoidance of the p-n junction eliminates or reduces the dark current associated with Shockley-Read defect-related processes, which are suppressed by the presence of carriers. However, it does not allow Auger processes to be suppressed via full depletion of the majority and minority carriers, as discussed above. Instead, the dominant diffusion dark current is suppressed by reducing the total thickness of the absorber.

Figure 6:
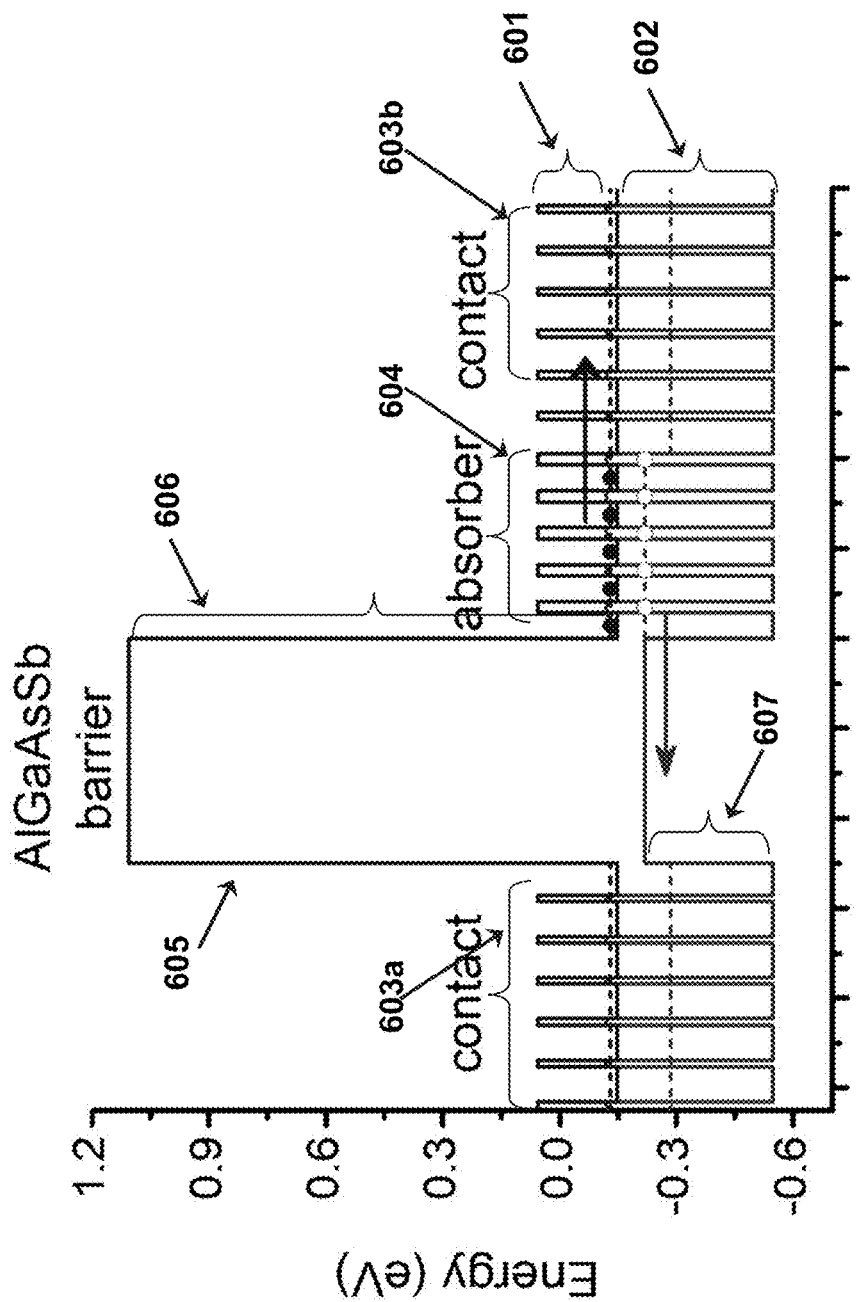
FIG. 6 is a plot illustrating energy band profiles and energy levels for an exemplary RCID having a thin absorber region and an nBn active core within a resonant cavity in accordance with the present invention.

The plot in FIG. 6 illustrates band profiles for an exemplary embodiment of an nBn active core for a long-wave infrared (LWIR) RCID in accordance with the present invention. The spatial dimensions in the figure are not drawn to scale. In this structure, the conduction and valence band edges 601 and 602, respectively, in the heavily-doped (typically $\approx 10^{17}$ cm$^{-3}$) contact regions 603a and 603b, and the less-heavily doped (typically unintentionally doped at $\approx 10^{15}$-$10^{16}$ cm$^{-3}$) absorber region 604 are shown in the FIGURE as solid lines, while the extremal energies of the quantum-confined subbands are indicated with dashed lines. The energy gaps in the contact regions are larger than in the absorber to suppress thermal generation.

The exemplary embodiment of an nBn active core for an RCID detector shown in FIG. 6, which is configured for detection at $\lambda$=12-13 μm at an operating temperature of T$\approx$60 K, uses an absorber with a band gap of 88 meV. The absorber superlattice (SL) 603 is designed to have some overall compressive strain, in order to increase the absorption coefficient by 60-65%. This would not be possible for a conventional absorber with a total thickness of several μm. In the exemplary embodiment described herein, the layer structure of the SL absorber 604 is 57 Å InAs/25 Å InAs$_{0.45}$Sb$_{0.55}$, with the absorber being background-doped with a density that typically ranges from $10^{15}$ to $10^{16}$ cm$^{-3}$, depending on the particular molecular beam epitaxial (MBE) system employed for the growth.

The absorbed fraction of incident light per period per pass ranges from 0.1% at $\lambda$=8 μm to 0.05% at 13 μm. Therefore, with an anti-reflection coating, a single pass through the 20-period, 164-nm-thick structure would result in 1-2% absorption.

The nBn structure also includes a 200-nm-thick Al$_{0.4}$Ga$_{0.6}$As$_{0.03}$Sb$_{0.97}$ barrier region 605 having valence and conduction bands 606 and 607, respectively, and a wider-gap (E$_g \approx$160 meV) n region 603a composed of a Ga-free 77 Å InAs/15 Å InAs$_{0.45}$Sb$_{0.55}$ SL with an intentional doping level $\approx 10^{17}$ cm$^{-3}$. Since it is difficult to contact the thin absorber directly, a heavily-doped contact layer 603b is also employed on the other side of absorber 604. The heavily n-doped contacts are designed to be essentially transparent to the light in the 8-13 μm spectral region. The AlGaAsSb barrier 605 may be either undoped or doped lightly p-type to reduce the band bending that would be induced by an n-type background. The nBn configuration should also completely suppress the surface leakage mechanisms characteristic of p-type InAs-containing narrow-gap layers, without requiring passivation or other measures.

One approach for constructing an RCID in accordance with aspects of the present invention having a bottom mirror with R$_2 \approx$1 employs a GaSb/AlAs$_{0.08}$Sb$_{0.92}$ quarter-wavelength stack that is grown by molecular beam epitaxy (MBE) on a GaSb substrate below the n-type region, with thin absorber QW(s) and a p-type region grown on top of the n-type region. To reduce the parasitic voltage drop at the heterointerfaces, the conduction-band discontinuity can be smoothed with a 10 GaSb/10 Al(As)Sb superlattice with approximately ten repeats and/or a higher doping level in the immediate vicinity of the heterointerfaces between each GaSb layer and the adjacent AlAs$_{0.08}$Sb$_{0.92}$ layers.

This approach was used by Dier et al., see "Reduction of hetero-interface resistivity in n-type AlAsSb/GaSb distributed Bragg reflectors," *Semicond. Sci. Technol.* 23, 025018 (2008), and has been implemented at the Naval Research Laboratory to minimize the electrical resistance of high-reflectivity bottom mirrors for interband cascade vertical cavity surface emitting laser (VCSEL) structures. In the case of an exemplary bottom mirror consisting of a 22.5-period GaSb/AlAsSb stack, a maximum reflectivity of 99.4% at $\lambda$=3.4 μm was calculated.

An RCID device may be formed by placing a thin absorber region in accordance with the invention within a resonant cavity such as the exemplary cavity configuration illustrated in FIG. 1, though it will be obvious to one skilled in the art that the features of the present invention may also be implemented in numerous other cavity configurations that accomplish resonant cavity detector operation. For example, the top (or bottom) mirror may be a dielectric Bragg mirror, a grown semiconductor Bragg mirror, a metal mirror, a hybrid that incorporates a combination of dielectric and/or semiconductor and/or metal layers, or some other mirror configuration known to the art.

The inventive designs and features described above for the absorber and surrounding regions may also be implemented in architectures wherein the photoexcitation propagates within the plane of the epitaxial structure rather than being vertically incident, i.e., parallel to the growth axis of the epitaxial structure, as in the case illustrated in FIG. 1. For example, the photoexcitation may be incident via a waveguide that originates elsewhere on a photonic integrated circuit (PIC) that may contain one or more optical sources and one or more resonant cavity detectors, as well as other optical and/or electronic components. The PIC substrate may be silicon, in which case the incident waveguide may be silicon-based while the waveguide in the absorber region may be a hybrid waveguide that shares the optical mode between a silicon-based underlayer and the layers comprising III-V materials that contain the active absorber. Another example is that the substrate may be a III-V semiconductor that contains one or more sources as well as one or more resonant cavity detectors. In some embodiments, the resonant cavity for the resonant cavity detectors may be formed using etching or some other known material processing technique to form in-plane Bragg mirrors. For Si-based PICS, such mirrors may be formed using standard CMOS processing.

Figure 7:
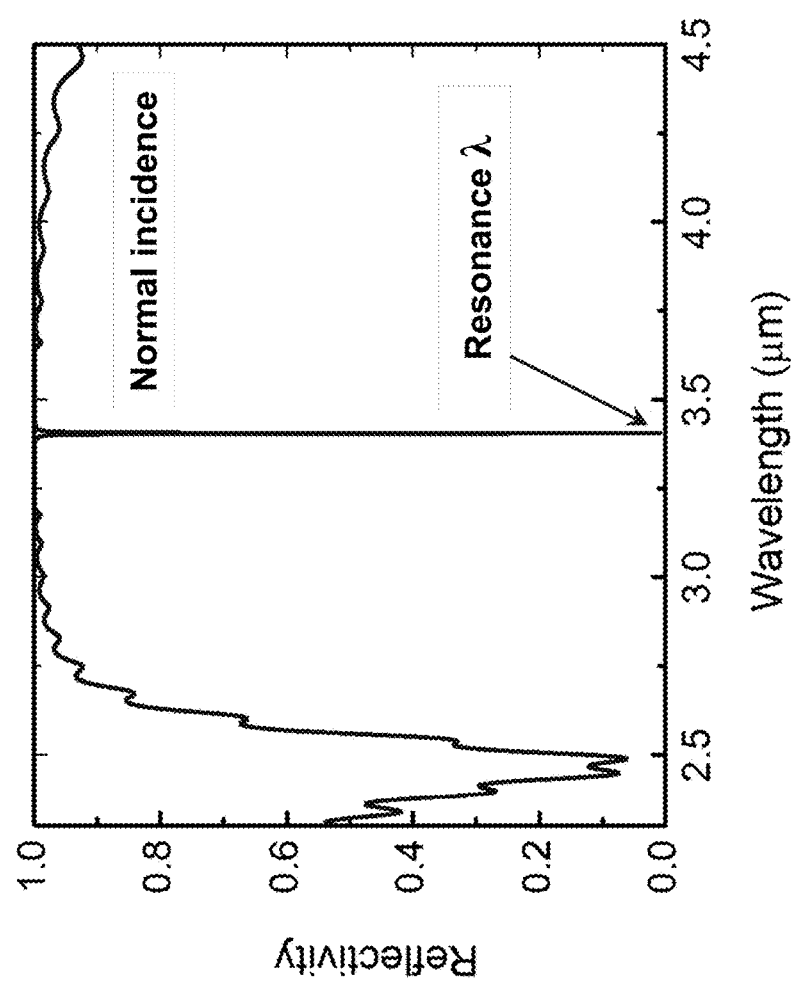
FIG. 7 is a plot depicting a reflection spectrum calculated for an exemplary RCID having a thin absorber region in accordance with the present invention.
Figure 8:
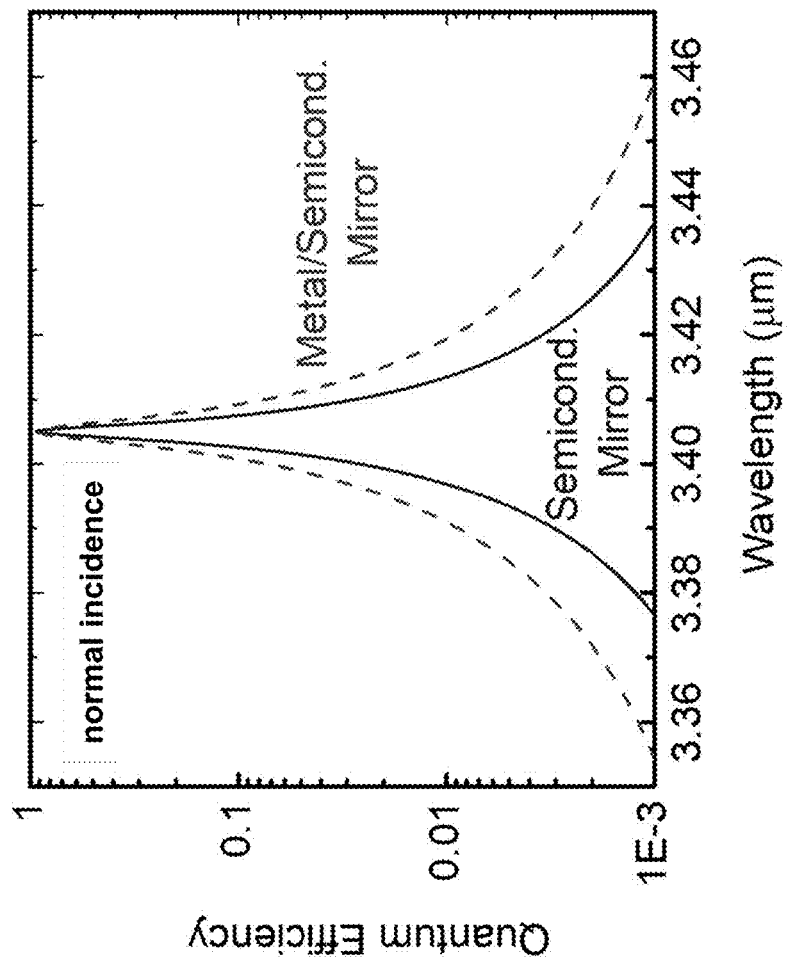
FIG. 8 is a plot depicting a quantum efficiency spectrum (assuming $\eta_c=1$) calculated for another exemplary RCID having a thin absorber region in accordance with the present invention.

The plots in FIGS. 7 and 8 illustrate the resonant enhancement of an exemplary RCID having a thin absorber region in accordance with the invention. The plot in FIG. 7 depicts the calculated reflection spectrum of radiation having a normal incidence on a device. While the reflectivity approaches unity over most of the 3-4.5-μm spectral band, it decreases nearly to zero at the resonance wavelength near 3.4 μm.

FIG. 8 illustrates the corresponding simulated quantum efficiency (QE) spectrum (assuming all of the photogenerated carriers are collected, i.e., $\eta_c=1$) for two exemplary RCIDs having semiconductor and hybrid bottom mirrors.

The solid curve in FIG. 8 shows the QE spectrum for an exemplary RCID having a 22.5-period GaSb/AlAsSb semiconductor bottom mirror, while the dashed curve shows the QE spectrum for an RCID having a hybrid bottom mirror comprising 3.5 periods of GaSb/AlAsSb on top of a layer of gold (dashed curve). The resonance of the RCID having a hybrid mirror is not as sharp as for one having the all-semiconductor mirror, because the reflectivity $R_2$ of the metal/semiconductor hybrid mirror is not as high.

At longer wavelengths, it becomes impractical to grow a highly reflective bottom mirror by the preferred epitaxial growth technique of MBE, because the total mirror thickness would significantly exceed 10 μm.

However, a high-reflectivity bottom mirror can still be realized by taking advantage of the refractive index decrease associated with the plasma effect in a heavily-doped semiconductor. In such a case, the magnitude of the plasma shift scales as $\lambda^2 N$, where N is the dopant concentration. An attractive choice for the heavily-doped material is $n^+$-$InAs_{0.91}Sb_{0.09}$, lattice matched to the GaSb substrate, which can be doped as high as $10^{19}$ cm$^{-3}$. For example, simulations project that at $\lambda=8.0$ μm, a hybrid bottom mirror comprised of a 6-period GaSb/AlAsSb stack grown on top of a 3-period GaSb/$n^+$-$InAs_{0.91}Sb_{0.09}$ stack will provide a reflectivity of 97.5%, even though the total epitaxial thickness is less than 10 μm.

In other embodiments, the bottom mirror can be formed by growing a thin semiconductor stack, removing the GaSb substrate, and then depositing a metal mirror (e.g., a 200-nm-thick layer of Au) on the bottom of the semiconductor stack (where the substrate had been).

A further advantage of an RCID in accordance with the present invention is that it provides multiple novel means for tuning the resonance wavelength following completion of the epitaxial growth of the structure. For example, the resonant cavity may intentionally be grown too short, after which its length is adjusted by adding a thin spacer film with variable thickness of Ge, Si, or some other low-loss material. Alternatively, the cavity may intentionally be grown too long, after which its length is adjusted by etching away some of the topmost epitaxial material. In both cases, the top dielectric mirror is subsequently deposited, as described above, to form a complete cavity whose resonance wavelength falls within the bandwidth of both top and bottom mirrors.

Figure 9:
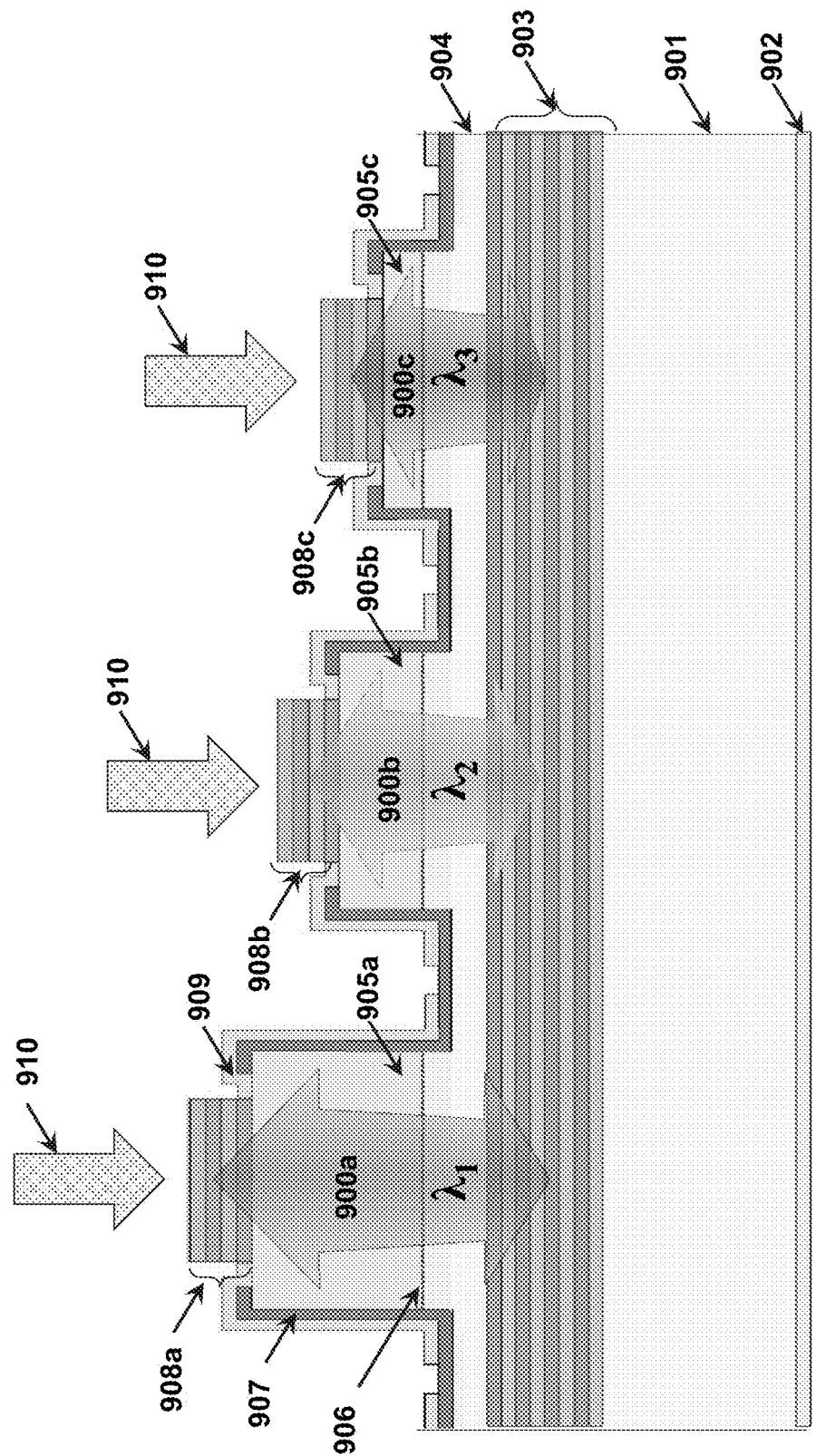
FIG. 9 is a block schematic illustrating multiple mesas with different resonance wavelengths for another exemplary resonant cavity infrared detector (RCID) having a thin absorber region in accordance with the present invention.

FIG. 9 illustrates an exemplary structure in which the cavity resonance is tuned by etching away some of the epitaxial material. Such a structure can include a bottom contact metallization layer 902 on a bottom surface of an n-GaSb substrate 901, a bottom n-GaSb/AlAsSb mirror 903, an n-InAs/AlSb superlattice n-region 904 and GaSb p-regions 905a/905b/905c, and dielectric top mirrors 908a/908b/908c, with the n- and p-regions separated by an InAs/GaInSb/InAs single-"W"-structured QW ultra-thin absorber 906 between the n- and p-regions. As in the resonant-cavity structure illustrated in FIG. 1, the detector mesas (which can be circular or square) is etched to below the absorber region 906, with an annular top metal contact 909 deposited around the perimeter of each circular or square mesa, and the mesa sidewalls and exposed region outside the mesa and below the junction (formed by the mesa etch) are coated with a dielectric 907 such as SiN before metallization of the top contact to prevent shorting of the junction. In operation, the RCID is illuminated by radiation 910 normally incident on top mirror 908a/908b/908c.

As described above, the bottom and top mirrors form resonant cavities which now provide different resonant wavelengths on the same chip because the cavity lengths are different. As noted above, in this embodiment, the effective length of each resonant cavity—and thus the resonance wavelength of each detector—can be tuned by etching away some of the epitaxial material to form resonant cavities 900a/900b/900c having respective p-type region thicknesses 905a/905b/905c. The multiple cavity thicknesses provide—an RCID having multiple resonant wavelengths $\lambda_1/\lambda_2/\lambda_3$ available on the same chip.

An RCID fabricated in accordance with aspects of this embodiment of the present invention may use this post-growth adjustment of the cavity length to fine-tune the cavity resonance to assure the sensitive detection of a precise target wavelength $\lambda_{target}$. Alternatively, the detection window can be tuned over multiple resonance wavelengths (tuning over >10 different wavelengths should be feasible). In some embodiments, the spacer thickness or etch depth for one or more of the mesas on a chip may be zero. Devices having multiple cavity lengths with multiple resonance wavelengths can be used to provide a reference signal at a wavelength not strongly absorbed by a substance being sensed, to provide broader spectral coverage for detecting multiple absorption lines, to compensate for thermal variations of $\lambda_{res}$, or to probe a broadband spectrum at multiple selected wavelengths to provide positive identification of an absorbing species.

Figure 10:
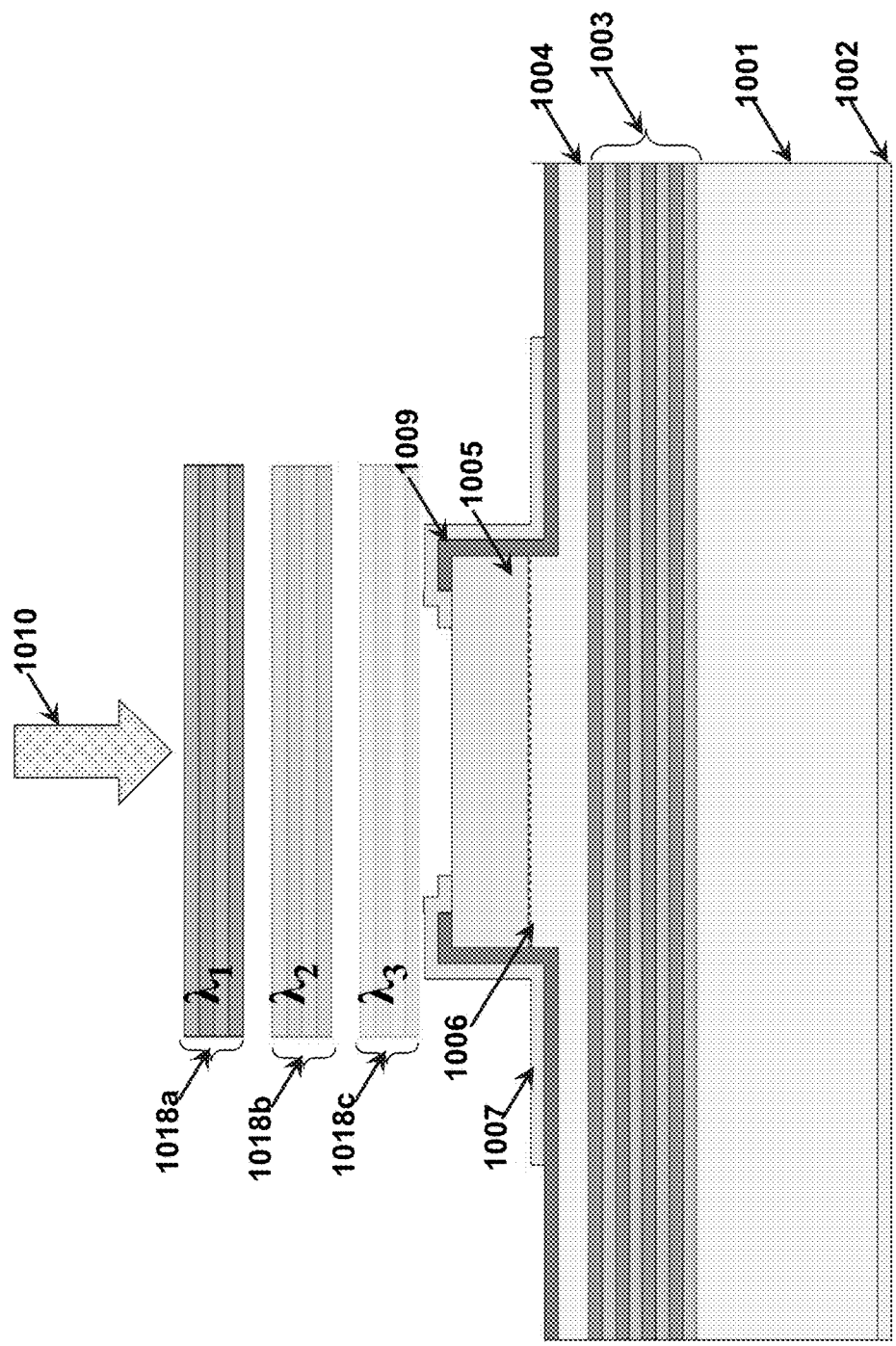
FIG. 10 is a block schematic illustrating the mesa and external mirror structure for another exemplary embodiment of an RCID having a thin absorber region in accordance with the present invention.

FIG. 10 schematically illustrates another exemplary embodiment of the invention, in which the top mirror is replaced by a metallic or dielectric mirror that is external to the semiconductor chip.

As with the other embodiment illustrated in FIG. 9, the exemplary RCID illustrated in FIG. 10 includes a bottom contact metallization layer 1002 on a bottom surface of an n-GaSb substrate 1001, a bottom n-GaSb/AlAsSb mirror 1003, an n-InAs/AlSb superlattice n-type region 1004 and GaSb p-type regions 1005, with the n- andp-type regions separated by a single-"W"-QW InAs/GaInSb/InAs ultra-thin absorber 1006 between the n- and p-type regions. As in the other embodiments, the detector mesa comprising the n- and p-type areas is etched to below the absorber region 1006, with an annular top metal contact 1009 deposited around the perimeter of the circular or square mesa, and the mesa sidewalls and exposed region outside the mesa and below the junction (formed by the mesa etch) are coated with a dielectric 1007 such as SiN before metallization of the top contact to prevent shorting of the junction.

However, instead of having a dielectric mirror such as dielectric mirror 608 that forms part of the resonant cavity, an RCID in accordance with this embodiment has a metallic or dielectric mirror 1018a/1018b/1018c that is external to the structure of the chip. The three mirrors depicted in the figure represent the same mirror tuned to three different positions that produce three different resonant wavelengths. A significant advantage of this approach is that the resonant wavelength can in principle be tuned continuously, via adjustment of the position of the top mirror. In operation, the RCID is illuminated by radiation 1010 normally incident on top of the external mirror.

Although the cavity becomes longer in this case, it can be made spectrally selective using an angle-adjustable grating or similar tuning element. Alternatively, a micro-positioning mechanism known to the art, such as a piezo-tunable MEMS mirror, can be used to dynamically tune the cavity length and thereby provide tuning of the spectrally selective feedback. See Felder 2007, supra. In both cases, the maximum spectral tuning range is again limited by the bandwidths of the semiconductor bottom mirror and the external top mirror.

In another example, the LWIR nBn design described above and illustrated in FIG. 6 may be incorporated into an exemplary RCID by employing a broadband metallic mirror having a reflectivity R>95% over the 8-13 µm range on the bottom of the absorber, following removal of the GaSb substrate. The top mirror in this exemplary embodiment is a two-layer high-reflection Ge/YF$_3$ coating (R=83-87% and very low absorption in the 8-13 µm range) having both layer thicknesses equal to $\lambda_c/4n$, where $\lambda_c$=9.9 µm is the center wavelength and n is the index in the layer in question.

The entire cavity has a net thickness of $\lambda_c/n$, with the absorber positioned at the antinode of the optical electric field at the center wavelength. As the wavelength shifts towards the edges of the spectral range, the antinode enhancement is reduced from 1.99 (close to the maximum possible value of 2) to ≈1.5. In order to make sure that the cavity length is correct regardless of the precise detector structure, high-index GaSb or Ge spacers are used between the active detector structure and the mirrors, if necessary.

The device structure is designed so that detection can be performed at wavelengths in the 8-13 µm range. This makes it possible to employ the present structure to detect multiple wavelengths by varying the cavity lengths with Ge spacers of the proper thickness or using external spectrally selective feedback. The cavity's resonance wavelength, $\lambda_{res}$, is determined by its effective length and the refractive indices of its constituent layers. The QE is enhanced significantly only if $\lambda_{res}$ falls within the high-reflectivity bandwidths of both top and bottom mirrors. We estimate that for a given cavity length, the RCID design specified above will produce a narrow resonance with high QE within ≈10 nm. More precisely, as the cavity length is changed the linewidth varies in the 10-15 nm range. The QE is projected to vary from 90% at $\lambda_{res}$=8 µm to 50% at 13 µm. A longer maximum wavelength of 13.5 µm can alternatively be accommodated using a similar cavity and mirror design, although at the expense of a lower operating temperature.

The top mirror in some embodiments of such an nBn detector can consist of a quarter-wave stack of largely transparent dielectrics having a large index contrast. Instead of Ge, other high-index materials without free carriers and phonon-related transitions in the LWIR can be used. YF$_3$ can be replaced by other rare-earth fluorides or different low-index materials transparent in this wavelength range. The broadband metal mirror can be replaced by a combination of a Bragg semiconductor mirror and a metal mirror with reduced spectral coverage. The most versatile embodiment employs an external top dielectric mirror whose position can be piezo-electrically tuned to vary the resonance wavelength.

In order to inject electrical current into the III-V semiconductor residing below the top mirror, the preferred embodiment uses a lateral contact, though other configurations may be used as appropriate. The material to which the contact is made may be a heavily doped n$^+$-InAs(Sb) layer grown on top of the p-type region. In preferred embodiments, the heavily doped contact layer is positioned at a node of the cavity electric field, in order to minimize the optical loss.

The RCID of the invention can be monolithically combined with a light-emitting device that is grown on the same substrate. In some cases, the light emission may come from a vertical-cavity laser, see A. Bachmann et al., "Single-mode electrically pumped GaSb-based VCSELs emitting continuous-wave at 2.4 and 2.6 µm," *New Journal of Physics* 11, 125014 (2009); and W. W. Bewley, C. L. Canedy, C. S. Kim, C. D. Merritt, M. V. Warren, I. Vurgaftman, J. R. Meyer, and M. Kim, "Room-temperature Mid-Infrared Interband Cascade Vertical-Cavity Surface-Emitting Laser," *Appl. Phys. Lett.* 99, 151108(2016), that employs the RCID semiconductor bottom mirror as its top mirror. In other cases, illumination can be from a broadband illumination source such as a light-emitting device, for example, based on an interband-cascade active region. See J. Abell, C. S. Kim, W. W. Bewley, C. D. Merritt, C. L. Canedy, I. Vurgaftman, J. R. Meyer, and M. Kim, "Mid-infrared interband cascade light emitting devices with milliwatt output powers at room temperature," *Appl. Phys. Lett.* 104, 261103 (2014). In the latter case, the resonant-cavity detector would provide spectral selectivity, for example, for chemical species identification, despite the use of a broadband light source. In some embodiments, the monolithic infrared light source and resonant-cavity detector can be used in conjunction with a fixed or position-tunable external top mirror to provide extremely sensitive detection of selected trace gas species present in the gap between the top of the semiconductor and the external top mirror.

The embodiments described above have employed MBE to grow the semiconductor components of the photodetector. IR detector structures may also be grown by other means, although to date the growth quality has not matched that achievable using MBE. Most of the embodiments discussed above are also readily adaptable, using design techniques well known to the art, to growth on an InAs substrate. The bottom mirror is then replaced by a lattice-matched combination such as GaAsSb/AlAsSb or InAs/AlAsSb for LWIR detectors, and the p-region, absorber, and n-regions are also modified accordingly to maintain strain-balancing to the lattice constant to InAs. Other embodiments employ another substrate and bottom mirror material, such as GaAs combined with a GaAs/AlGaAs mirror. The GaSb-based IRp-n junction, nBn, and absorber regions are then grown using metamorphic techniques known to the art.

In some embodiments, the optical input to the RCID can be temporally modulated, e.g., by an external electro-optical modulator or mechanical chopper. When combined with lock-in analysis of the detected signal, this will provide further discrimination against non-optical noise sources such as diffusion, generation-recombination, and surface leakage dark currents.

In various embodiments, the invention may be used to construct high-sensitivity narrow-bandwidth single element detectors, arrays of detectors with a selected range of resonance wavelengths, or imaging arrays for narrow-band imaging. Other embodiments obtain hyperspectral imaging by employing a position-tunable external mirror in conjunction with the RCIC array.

In other embodiments, the RCID of the invention is used to enhance the speed of a single-element detector, small array with multiple resonance wavelengths, or imaging array, by taking advantage of the much shorter time required to extract minority carriers from the ultra-thin absorber, as compared to the longer time required for diffusion across the much thicker absorber of a convention IR detector.

In other embodiments of a resonant-cavity infrared photodetector with fully-depleted absorber in accordance with the present invention, the propagation of the optical signal to be detected occurs in the plane of the epitaxial structure rather than along its growth axis.

The in-plane interband absorption coefficient is $\alpha = \Gamma\alpha_0 + \alpha_i$, where $\alpha_0$ is the material interband absorption coefficient, which was employed above in analyzing the case of vertical light propagation, $\alpha_i$ is any parasitic absorption or scattering in the waveguide that does not produce photoexcited carriers in the absorber, and $\Gamma$ is the optical confinement factor, which represents the vertical overlap of the optical mode with the absorber layer (more specifically, the fraction of the integrated square of the optical electric field that lies within the absorber material). As discussed above, a very thin absorber is suitable for full depletion of the majority and minority carriers without requiring a large bias voltage to induce carrier sweep-out. For the laterally propagating light, the net absorbance A per pass is then $A = \alpha L_p$, where $L_p$ is the lateral path length of the absorber region.

The quantum efficiency (QE) for detection within the lateral resonant cavity is given by the relation in Equation (3), supra, multiplied by an additional factor of $\Gamma\alpha_0/\alpha$ to account for any losses that result from parasitic loss within the waveguide. The resulting detectivity is given by the relation in Equation (1), supra, with the diffusion-limited dark current given by the relation in Equation (2), supra.

It will usually be advantageous for the in-plane optical signal to propagate within a waveguide that is narrow enough to provide propagation in a single lateral mode. In some embodiments, the waveguide may be formed entirely within the III-V semiconductor epitaxial layer that provides the active absorber, while in other embodiments the optical signal may propagate in a hybrid waveguide that is formed by bonding the III-V material to silicon or some other low-loss waveguide material formed on a suitable substrate. For example, see S.-H. Hsu, "Reflectively Coupled Waveguide Photodetector for High Speed Optical Interconnection," *Sensors* 10, 10863 (2010); M. Muneeb et al., "III-V-on-silicon integrated micro-spectrometer for the 3 μm wavelength range," *Opt. Expr.* 24, 9465 (2016); R. Wang et al., "III-V-on-Silicon Photonic Integrated Circuits for Spectroscopic Sensing in the 2-4 μm Wavelength Range," *Sensors* 17, 1788 (2017).

When the optical signal propagates in the plane in such a device, the QE of the photodetector can generally be optimized by configuring the detector such that it has a lateral propagation length long enough to absorb most of the photons.

Because the lateral extent of the active absorber region can be very long, high QE can be obtained even when the absorber region is very thin. In particular, the detector can have a high QE when the absorber is thin enough to realize full carrier depletion at a low bias voltage, when the absorber constituents are so highly strained or non-lattice-matched that relaxation would occur if the absorber region were thicker, or when the other novel absorber designs discussed above are employed. The absorber can also be formed from a material with relatively low minority-carrier mobility, since the required diffusion length to collect the minority carriers scales with the absorber thickness. These advantages may be realized even when the in-plane waveguide or another propagation region does not form a resonant cavity, which can be obtained, for example, by bounding it with high-reflectivity mirrors.

As is well known to the art, in-plane light propagation can be achieved using mirrors that provide high reflectivity within the waveguide, e.g., by patterning distributed Bragg reflectors (DBR) gratings into the lateral waveguide in which the light propagates. For example, see M. Ariga et al., "Low Threshold GaInAsP Lasers with Semiconductor/Air Distributed Bragg Reflector Fabricated by Inductively Coupled Plasms Etching," *Jpn. J. Appl. Phys.* 39, 3406 (2000). It is also possible to tune the resonance wavelength of the DBR mirrors, using several methods known to the art. For example, see M. Okuda et al., "Tunability of Distributed Bragg-Reflector Laser by Modulating Refractive Index in Corrugated Waveguide, *Jpn. J. Appl. Phys.* 16, 1501 (1977); and U.S. Pat. No. 9,209,601 to S. Davies et al., "Monolithically Integrated Tunable Semiconductor Laser." Other methods known to the art may also be used to form mirrors that reflect light propagating in the plane.

However, for in-plane propagation, the dark current increases linearly with the lateral length of the propagation region. Therefore, as in the case of light propagation along the vertical direction, i.e., outside the plane of the detector, the dark current for detection within a narrow spectral band can be reduced by forming a resonant cavity to provide multiple passes of the optical signal, e.g, by providing reflectors on opposite ends of the detector, which substantially shortens the detector length required to realize high QE and a high detectivity D*. In addition, as in the case of vertical light propagation discussed above, such a resonant cavity substantially narrows the spectral bandwidth of the detected signal. All of the design options discussed above for the case of a very thin absorber incorporated into a resonant cavity along the vertical axis may also be applied to the design of detectors with very thin absorbers that are incorporated into an in-plane resonant cavity so that the in-plane RCIDs can also provide high QE when the absorber is very thin.

In some embodiments of this aspect of the present invention, the optical signal can propagate within a hybrid waveguide that includes an RCID photodiode as part of a photonic integrated circuit (PIC) configured to detect an optical signal propagating along the plane of the epitaxial structure. Such a PIC in accordance with the present invention may be formed on a silicon, germanium, chalcogenide, III-V, or other suitable waveguide platform known to the art. For example, see G.-H. Duan et al., "Hybrid III-V on Silicon Lasers for Photonic Integrated Circuits on Silicon," *IEEE J. Sel. Topics Quant. Electron* 20, 6100123 (2014); A. Spott et al., "Heterogeneous Integration for Mid-Infrared Silicon Photonics," *IEEE J. Sel. Topics Quant. Electron.* 23, 8200818 (2017); P. Ma et al., "Low-loss chalcogenide waveguides for chemical sensing in the mid-infrared," *Opt. Expr.* 21, 29927 (2013); B. Schwarz et al., "Monolithically integrated mid-infrared lab-on-a-chip using plasmonics and quantum cascade structures," *Nat. Commun.* 5, 4085 (2014); S.-H. Hsu, "Reflectively Coupled Waveguide Photodetector for High Speed Optical Interconnection," *Sensors* 10, 10863 (2010). Suitable methods for fabricating such a structure are discussed, for example, in A. W. Fang et al., "Integrated AlGaInAs-silicon evanescent racetrack laser and photodetector," *Opt. Expr.* 15, 2315 (2007).

Figure 11A:
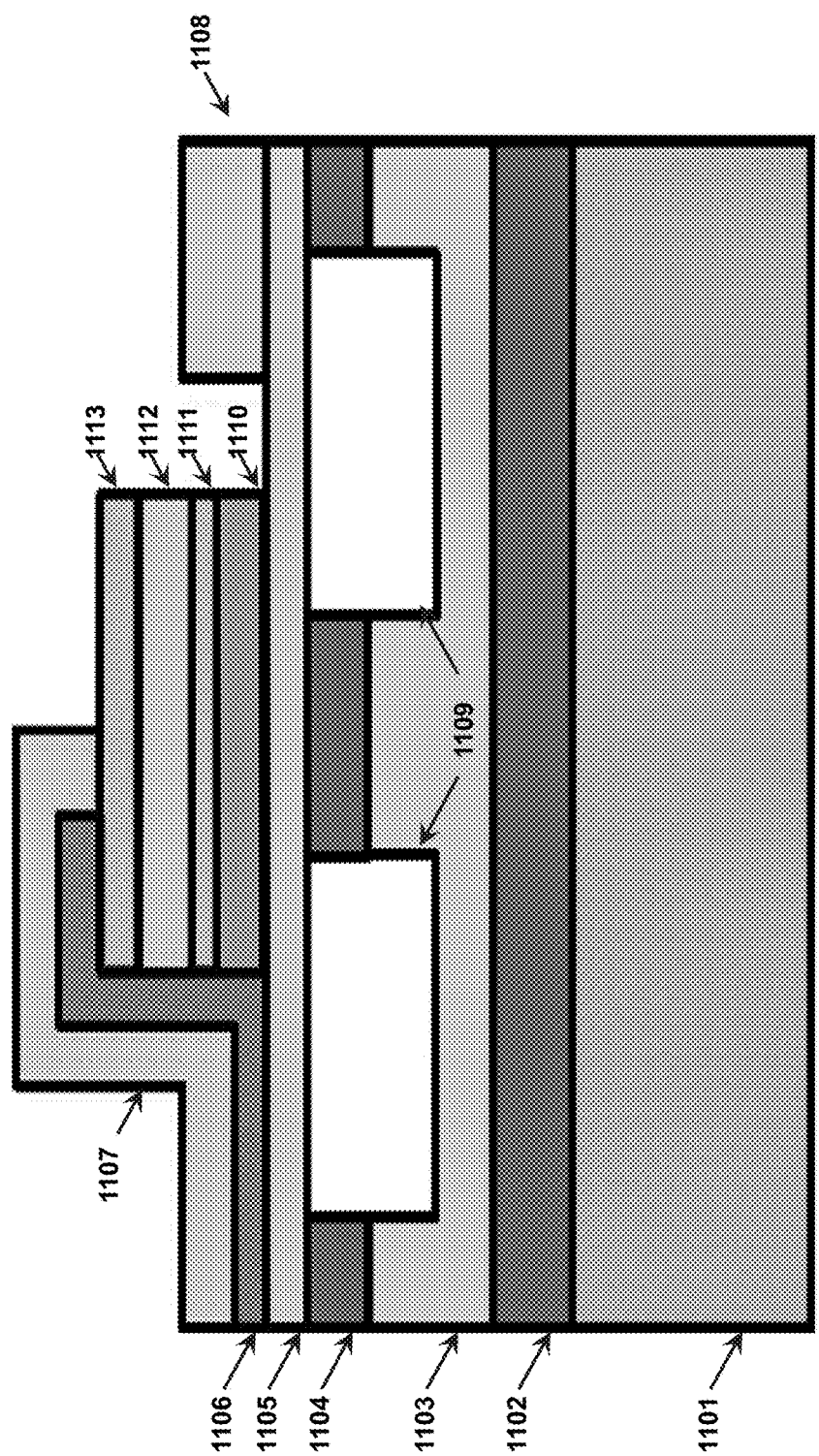
FIGS. 11A and 11B are block schematics illustrating aspects of exemplary embodiments of a hybrid waveguide that includes a III-V RCID configured to detect an optical signal propagating along the plane of the epitaxial structure.
Figure 11B:
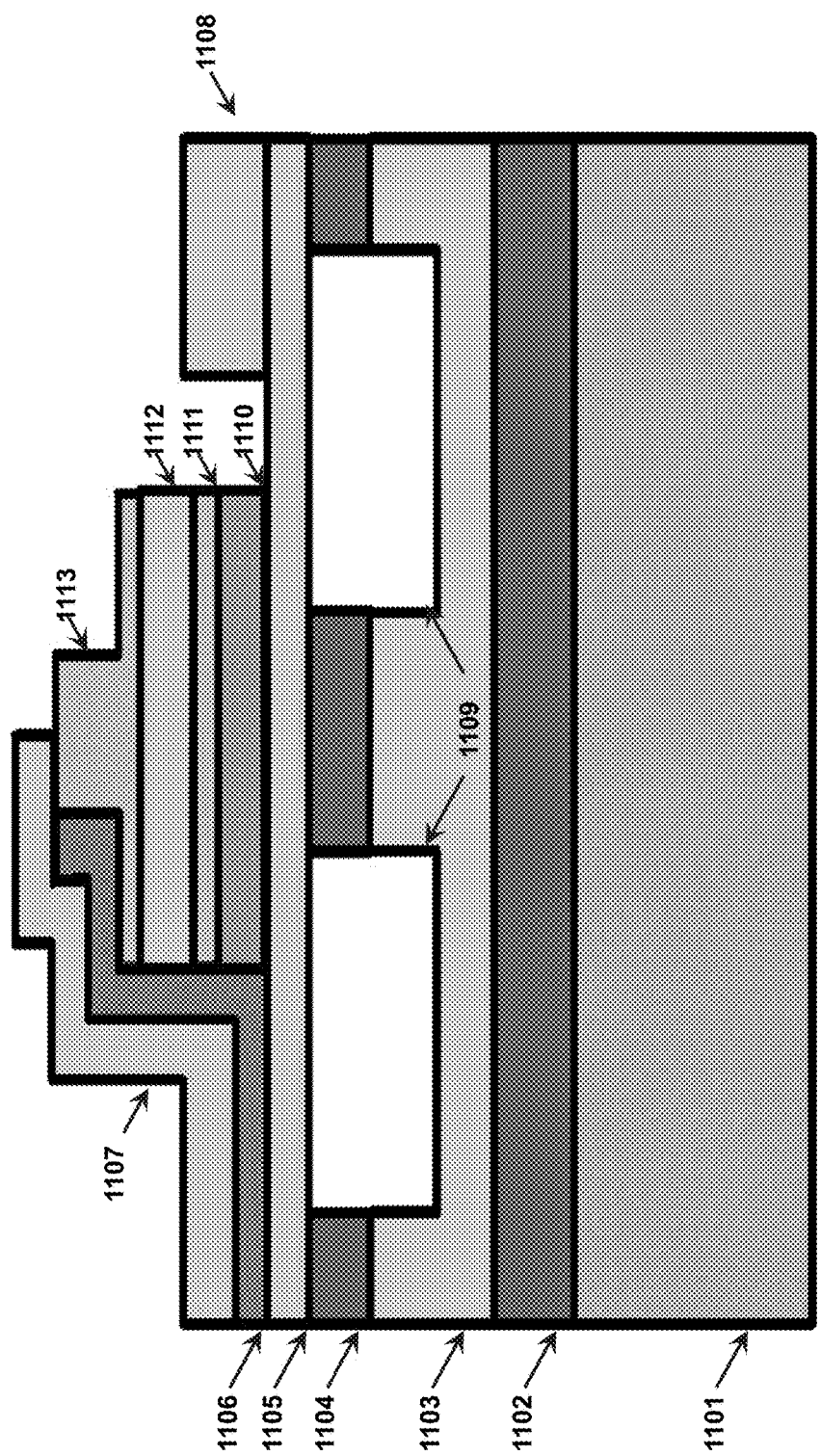

The block schematics in FIGS. 11A and 11B illustrate exemplary embodiments of such a hybrid waveguide in accordance with these aspects of the present invention. It will be noted that the configurations illustrated in FIGS. 11A and 11B are exemplary only, and numerous alternative III-V or hybrid waveguide configurations, as well as other materials and layering configurations in the III-V active detector structure, may also be employed within the spirit of the invention.

In the embodiments illustrated in FIGS. 11A and 11B, the hybrid waveguide is formed when a III-V chip containing the active components of an RCID photodiode is bonded to a pre-processed silicon portion of the waveguide.

This silicon portion of a hybrid waveguide in accordance with the present invention comprises a silicon wafer 1101, a first, lower SiN cladding layer 1102, and a silicon portion of the core 1103. In some embodiments, it may be advantageous to adjust the coupling of the optical mode propagating in the waveguide to the active absorber. For this reason, as illustrated in FIG. 11, an optional second cladding layer 1104 can be interposed between the top of the silicon portion of the waveguide and the bottom of the III-V portion of the waveguide, where the second, interposed cladding layer can be composed of SiN or some other material that has a lower refractive index than silicon and low optical loss in the wavelength region of interest. The silicon portion of the hybrid waveguide 1103 and optional SiN interposed cladding layer 1004 may be patterned to include one or more air or dielectric regions (such as air pockets) 1109 on each lateral side of the hybrid wavegide which can help to laterally confine the optical mode propagating in the hybrid waveguide and ensure that propagation is in a single lateral mode.

The RCID photodetector in a hybrid waveguide in accordance with the present invention is in the form of a III-V heterostructure comprising elements 1105, 1110, 1111, 1112, and 1113 described in more detail below. Thus, the RCID photodetector includes an $n^+$-InAs/AlSb superlattice or $n^+$-InAsSb bottom contacting layer 1105 disposed on top of the silicon portion of the core 1103 (or on top of the SiN interposed cladding layer 1104 if present), an $n^+$-InAs/AlSb superlattice n-region 1110 disposed on top of one or more first areas of an n+ superlattice layer 1105, a thin active absorber region 1111 (which may employ one of the designs discussed above or some other design) disposed on top of n-region 1110, a $p^-$-GaSb p-region 1112 disposed on top of active absorber region 1111, and a $p^+$-GaSb top contact layer 1113 disposed on top of p-region 1112. A bottom metal contact pad 1108 is disposed on top of one or more second areas of n+ superlattice layer 1105. The p-type GaSb used in this exemplary embodiment has favorable properties for the p-region and p+ contact layers of an RCID whose absorber contains Ga, e.g., is InAs/Ga(In)Sb or InAs/Ga(In)Sb/InAs/AlSb. However when the absorber does not contain Ga, e.g., is InAs/InAsSb or InAs/InAsSb/InAs/AlSb, it is more favorable to use a material or combination of materials with a lower valence band, such as the p-GaAl(As)Sb alloy, for the p-region and p+ contact layers of the detector.

In other embodiments of the invention, the structure illustrated in FIGS. 11A and 11B can be flipped, such that the n-region is on top and the p-region is on the bottom. In such alternative embodiments, the same schematic structure shown in FIG. 11A (or FIG. 11B) may be employed, where the bottom contacting layer 1105 is a p+ contacting layer such as $p^+$-GaSb, $p^+$-GaAl(As)Sb, or some other suitable, material, rather than an n+ contacting layer; 1110 is a p-region, which may be p-GaSb, p-GaAl(As)Sb, or some other suitable p-type material, rather than an n-region; 1111 is again the thin active absorber region; 1112 is an n-region, which may be an n-InAs/AlSb superlattice or some other suitable n-type material, rather than a p-region; and 1113 is an $n^+$ top contacting layer, which may be of an $n^+$ superlattice, $n^+$-InAsSb, or some other suitable $n^+$ material, rather than a $p^+$ contacting layer.

The waveguide structure further includes a dielectric layer 1106 disposed on top of one or more third areas of $n^+$ or $p^+$ layer 1105 and along at least one side of the III-V core of the waveguide, and further includes a top metal contact pad 1107 disposed on top of dielectric layer 1106, and extending to a top of $p^+$ or $n^+$ top contact layer 1113 to form a top contact pad. The optical mode for the light propagating in the plane of the structure and within in the hybrid waveguide often resides primarily within the silicon portion of the hybrid waveguide, although some fraction of the mode overlaps the III-V portion of the hybrid waveguide where it is detected. As in the embodiments described above for detecting light that propagates vertically rather than within the epitaxial plane of the structure, any photons absorbed in the III-V absorber region of the photodiode, which in this case resides in the III-V region of the hybrid waveguide, create a photocurrent signal when an appropriate bias is applied to the top and bottom contacts.

In some embodiments, the overlap of the optical mode, which often has its greatest concentration in the silicon portion of the waveguide, with the III-V absorber region can be tuned to an optimal value by adjusting the thickness of the interposed SiN or another cladding layer. In other embodiments, the optical mode overlap with the absorber region can be tuned by adjusting the width of the passive waveguide below the III-V active material. Such an adjustment of the overlap may be advantageous, for example, in cases where a resonant cavity is formed by placing high-reflectivity mirrors on each end of the active absorber length in the plane, or by placing the detector within a ring resonator as discussed below.

The maximum quality-factor (Q) of the cavity and the minimum linewidth of the absorption resonance will be limited by the absorbance per pass of the optical signal. Therefore, it may be necessary to reduce the absorbance per pass if high Q and narrow linewidth are to be realized with a reasonable cavity length. In other embodiments, the core of the silicon-based waveguide may employ Ge or a SiGe alloy having low loss in the wavelength region of interest. Silicon may then be used as the interposed and lower cladding material, since it has a lower refractive index than (Si)Ge, although other materials may also be employed.

As illustrated in FIG. 11A, in many embodiments, the top contact metal 1107 should be as narrow as possible (much narrower than the top of the ridge) in order to minimize parasitic losses resulting from overlap of the propagating optical mode with the top contact metal while still providing adequate electrical contact and remaining practical to fabricate by the preferred process using, e.g., optical or e-beam lithography.

A suitable top cladding layer with low refractive index, such as p-Al(Ga)AsSb if the p-region is on top of the photodiode or an n-InAs/AlSb superlattice if the n-region is on top, can be grown above the active detector layers 1110-1112 in some cases to minimize mode penetration into the top contact metal. In such cases, the $p^+$ or $n^+$ top contacting layer 1113 is grown on top of the top cladding layer to provide electrical contact with the top metal.

In other embodiments, such as that illustrated in FIG. 11B, the mode can be confined at the top of the hybrid waveguide by growing the $p^+$ or $n^+$ top contacting layer 1113 to a greater thickness, and then etching most of it (down to a depth that still allows sufficient current spreading across the width of the hybrid waveguide) to a much narrower ridge width (e.g., 1-2 μm) than the rest of the III-V portion of the hybrid waveguide. The narrowness of the top portion of the hybrid waveguide will then suppress optical penetration into the metal layer 1107 that resides on top of that layer. In that embodiment, the top metal contact layer should still be as narrow as possible.

A hybrid waveguide that incorporates a high-performance RCID photodiode that detects an in-plane optical signal propagating in a waveguide in accordance with the present invention can be used as the detection element of a compact on-chip chemical sensing package that can be used, for example, to sense trace chemical species in a gas sample.

The block diagrams in FIGS. 12A-12D and FIG. 14 schematically illustrate an exemplary embodiment of a chemical sensing system incorporating a hybrid waveguide in accordance with the present invention. As described in more detail below, a chemical sensor in accordance with one embodiment of the present invention includes a series of silicon-based ring resonators that provide sensing via evanescent coupling to a sample gas incident on the resonators in the area designated "sensing area" and a series of hybrid waveguides incorporating RCID photodiodes that receive light from the output of each ring resonator in the area designated "detection area," where the resonance wavelength of each RCID photodiode is matched to that of the ring resonator from which it receives light.

In some embodiments, such as the embodiment illustrated in FIG. 12A described below, the sensing area and the detection area are spatially distinct, with the ring resonators being formed from silicon-based waveguides that feed their output light into hybrid waveguides having RCID photodiodes incorporated therein. In other embodiments, such as the embodiment illustrated in FIG. 14 described below, the sensing area and the detection area are combined, with the ring resonators being formed from the hybrid waveguides themselves. In either case, such optoelectronic elements may be integrated on the same silicon chip, as discussed, for example, in Muneeb et al., supra and Wang et al., supra; see also M. J. R. Heck et al., "Hybrid Silicon Photonic Integrated Circuit Technology," *IEEE JSTQE: Semiconductor Lasers* (2013); and U.S. Pat. 9,612,398 to I. Vurgaftman et al., "Ultra-Broadband Photonic Integrated Circuit Platform." On-chip chemical sensing systems such as those illustrated in FIGS. 12 and 14 can be suitable for mass production of hundreds or thousands of sensors on the same chip. The individual sensors can then be singulated to provide a package that is both extremely compact and extremely inexpensive.

Figure 12A:
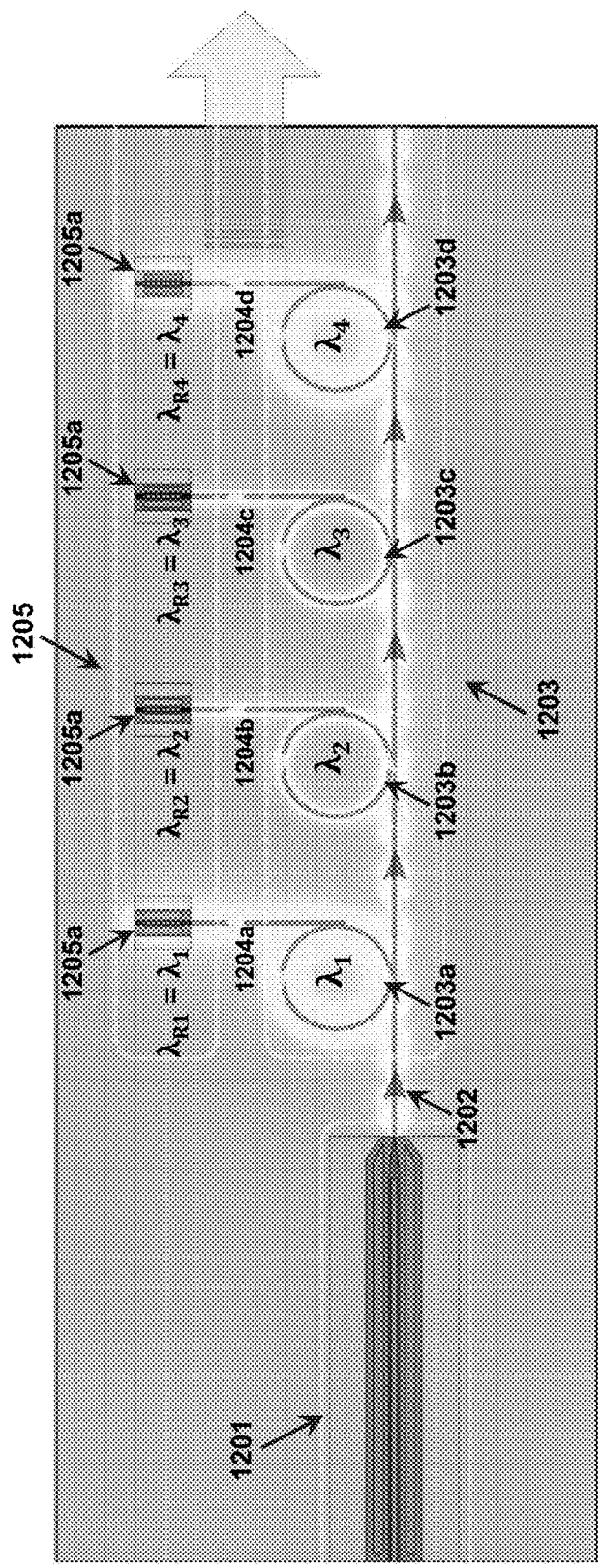
FIGS. 12A-12D are block schematics illustrating aspects of an exemplary embodiment of a chemical sensor including a hybrid waveguide incorporating an RCID photodiode configured to detect an optical signal propagating along the plane of the epitaxial structure in accordance with the present invention.

The block schematics in FIGS. 12A-12D illustrate aspects of a first exemplary embodiment of such a chemical sensor in accordance with the present invention. As illustrated in FIG. 12A, such a sensor can include an IR source 1201, a sensing area 1203, and a detection area 1205, all of which reside on a single chip. In such a sensor, an IR source output beam, i.e., IR light output from IR source 1201, is coupled into a suitable silicon-based waveguide such as an $Si/SiO_2$ waveguide 1202 and then propagates through the waveguide to sensing area 1203, which comprises a series of N silicon-based ring resonators 1203a, 1203b, 1203c, 1203d, etc. In the embodiment shown in FIG. 12A, each of the ring resonators is formed in a circular shape so as to form a ring cavity within the waveguide, though other closed loop shapes, e.g., oval or racetrack shapes, can be used so long as there is low bending loss and a high Q within the ring cavity. Each ring has a slightly different propagation length per pass (determined by the diameter in the case of a circular ring) and corresponding resonance wavelength $\lambda_1, \lambda_2, \lambda_3, \lambda_4$, etc., so that each ring selectively extracts light at its resonance wavelength from the IR source output beam as it travels through waveguide 1202 past the ring.

As described in more detail below, the light extracted from each of the N ring resonators travels through corresponding waveguides 1204a, 1204b, 1204c, 1204d, etc., and is then input into N corresponding hybrid waveguides 1205a, 1205b, 1205c, 1205d etc. residing in detection area 1205 of the same chip. Each of the hybrid waveguides has an RCID photodiode 1230 having a thin absorber layer incorporated therein, wherein the RCID photodiode configured to receive and process light propagating along the epitaxial plane of the waveguide.

Figure 12B:
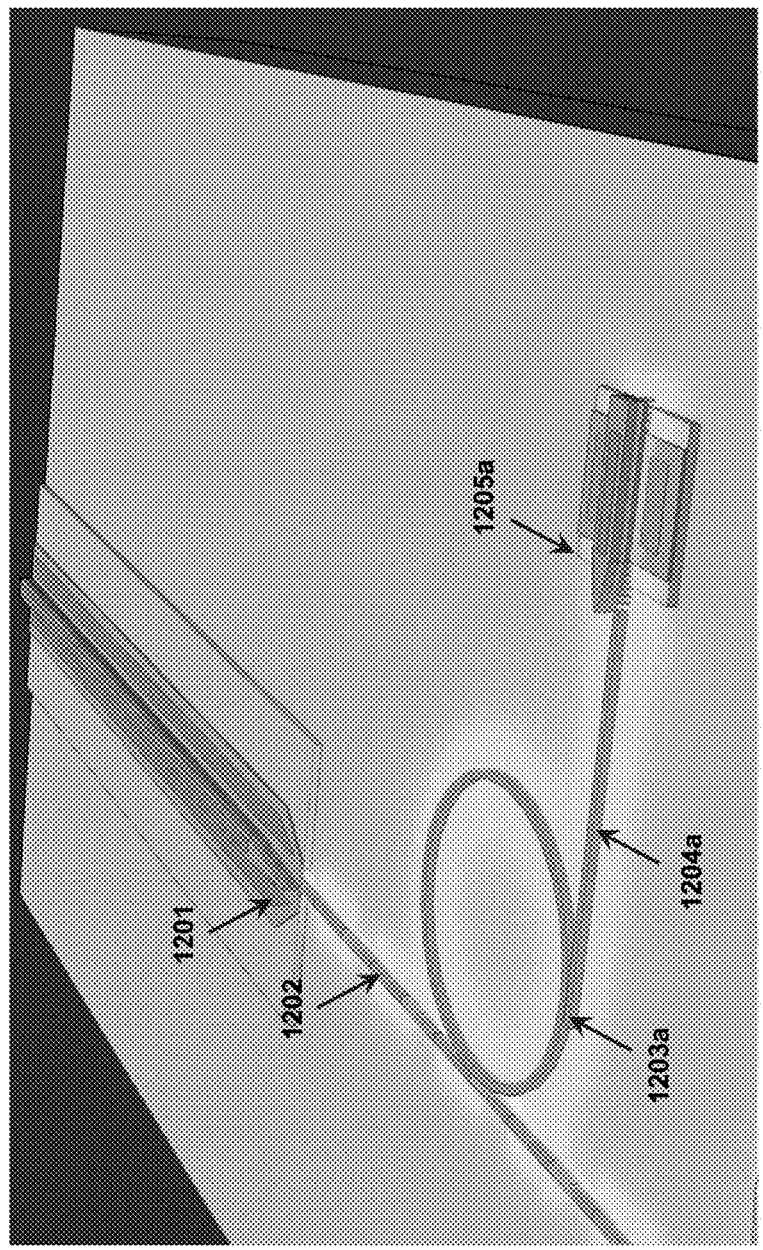
Figure 12C:
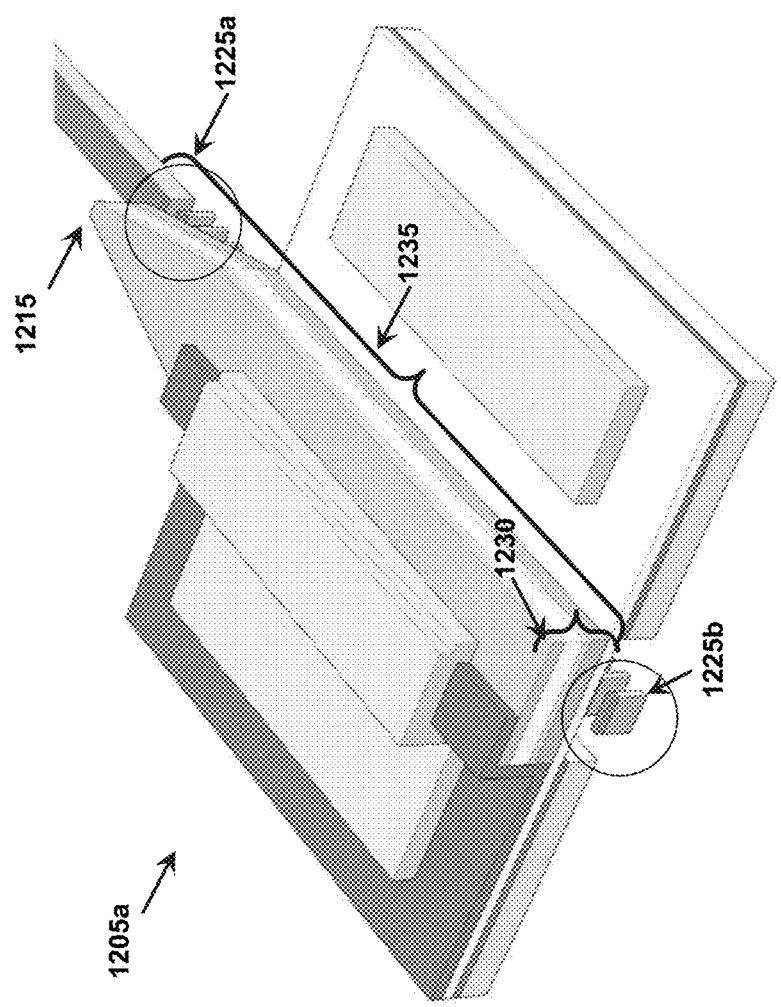
Figure 12D:
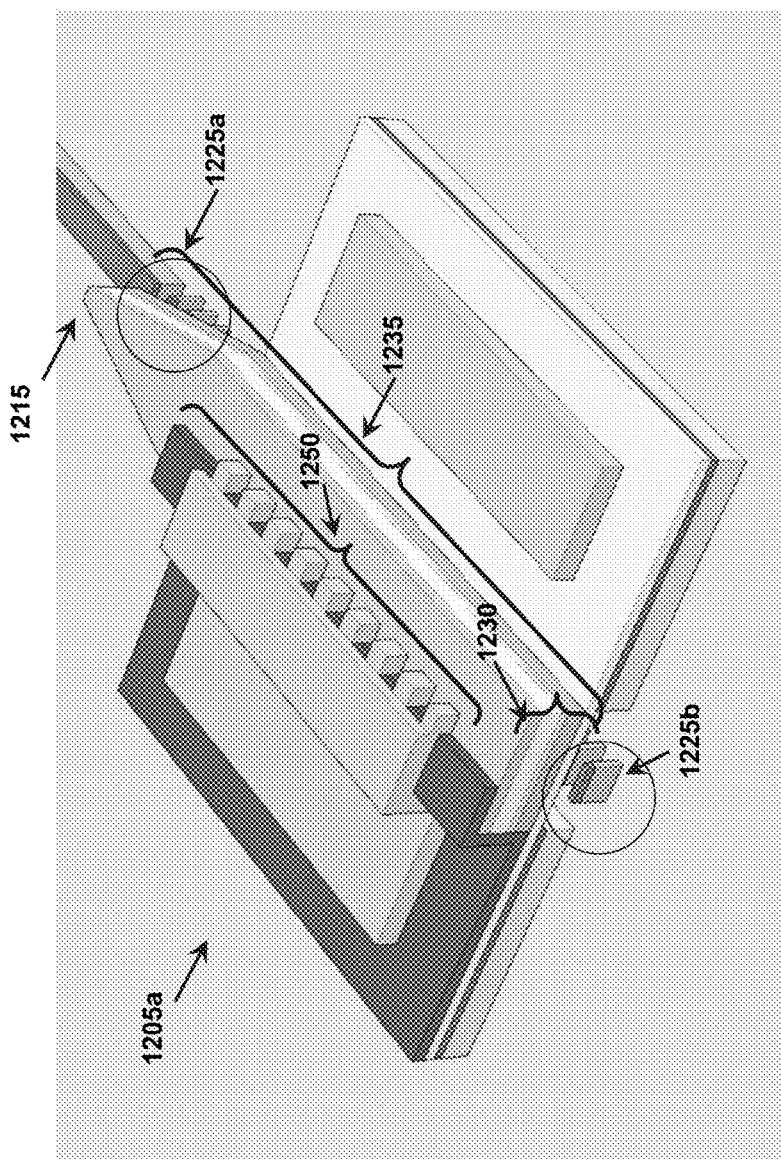

FIGS. 12B, 12C, and 12D further illustrate aspects of the chemical detector and hybrid waveguide in accordance with this embodiment of the present invention. As illustrated in FIG. 12B, 12C, and 12D, the hybrid waveguide 1205a has a tapered end 1215 configured to efficiently couple the optical signal from silicon waveguide 1204a and guide the signal into the hybrid waveguide that contains the RCID photodiode 1205a. The use of tapers to efficiently transfer optical modes that propagate in the plane between a silicon waveguide and a III-V/silicon hybrid waveguide is discussed, e.g., in A. Spott, E. J. Stanton, N. Volet, J. D. Peters, J. R. Meyer, and J. E. Bowers, *IEEE J. Sel. Topics Quant. Electron.* 23, 8200818 (2017), "Heterogeneous Integration for Mid-Infrared Silicon Photonics." In many embodiments, the efficiency for coupling from the silicon-based waveguide into the hybrid waveguide will be high, in part because in those embodiments most of the mode in the hybrid waveguide resides in the lower silicon portion of the waveguide, hence addition of the upper III-V portion of the hybrid waveguide will induce only a relatively small perturbation of the optical mode profile when the propagating optical mode transfers from the silicon-based waveguide to the hybrid waveguide.

As illustrated in FIG. 12D, the hybrid waveguide further includes DBR mirrors 1225a/1225b at both ends of the RCID photodiode 1230. The DBR mirrors 1225a/1225b form a resonant cavity 1235 that includes the detector, where the resonant cavity substantially enhances the quantum efficiency of the detector due to the multiple passes that the received light makes through the section of the cavity that includes the absorber.

Each of the RCIDs 1205a etc. has a corresponding resonance wavelength $\lambda_{R1}$, $\lambda_{R2}$, $\lambda_{R3}$, $\lambda_{R4}$, etc., with the resonance wavelength of each RCID being tuned to match the resonance wavelength of the corresponding ring resonator that couples into that detector. Matching the resonance wavelengths of the ring resonator and the detector may be aided, for example, by separate temperature tuning of the two regions of the device. In such a case, the resonance enhancement of D* in the RCIDs at a given operating temperature takes full advantage of the spectrally-narrow output of the ring resonators. This is especially critical in the context of on-chip chemical sensing, e.g., from a gas source, since this architecture relies on direct physical contact between the gas sample and the on-chip sensing area, which would be impractical if the on-chip detector were to require cryogenic cooling.

As described above, the RCID photodiode in the hybrid waveguide includes an active absorber which is configured to detect light at the resonance wavelength $\lambda_{R1}$, $\lambda_{R2}$, $\lambda_{R3}$, $\lambda_{R4}$, etc., of the particular RCID. The active absorber can be in any suitable form. In some embodiments this active absorber component employs an antimonide-based III-V material. In other embodiments, the active absorber may be a silicon bolometer, which may be advantageous at longer wavelengths (e.g., beyond 7 μm) for which a III-V detector material may have reduced sensitivity when the sensing system is operated at a non-cryogenic temperature.

In some embodiments of the invention, the infrared detector has a majority-carrier barrier configuration with a thin absorber region, i.e., an nBn or pBp configuration such as that discussed above with respect to FIG. 6. In such embodiments, layers 1110-1113 in FIGS. 11A and 11B are the appropriate layers known in the art to be used for an nBn or pBp detector, rather than the layers suitable for a photodiode. Detectors with an nBn or pBp configuration are then suitable for use as detectors 1205a, 1205b, 1205c, etc., in the on-chip sensor that is illustrated schematically in FIG. 12A-12D.

In operation, the top and/or sides of each ring 1203a, etc. are exposed to the gas sample to be tested, so as to allow evanescent coupling of the optical beam propagating in the ring to the gas sample. The resonance wavelengths $\lambda_1$, $\lambda_2$, $\lambda_3$, $\lambda_4$, etc., of the N ring resonators in the sensing area may be designed to match or not match (to provide reference signals) the absorption lines of one or more gas species of interest. It should be noted that while in some embodiments, the resonance enhancement and linewidth narrowing of the optical signal propagating in the sensing area are provided by ring resonators such as those depicted in FIG. 12A, in other embodiments, the resonance enhancement and linewidth narrowing of the optical signal propagating in the sensing area can be provided by any another suitable resonant cavity configuration, such as a linear cavity bounded by mirrors, where the sensing area resides within a resonant cavity formed by placing mirrors on both sides of the propagation pathlength of the sensing area. In other embodiments, the optical signal to be sensed makes a single pass through the sensing area and does not enter a resonant cavity.

If none of the gas species in the gas sample absorbs at the resonance wavelength of a given ring, the output from that ring resonator is unattenuated when it is input into its corresponding RCID. On the other hand, if the sample gas contains a gas species that absorbs light at the ring's resonance wavelength, the output from that ring is reduced by an amount related to the concentration of the absorbing gas species, and the net output from that ring resonator (and thus the input to its corresponding RCID) reflects that reduction. The optical beam from the IR source can make many round-trip passes around the high-Q ring cavity, with the absorption (if any) of light by the gas being significantly enhanced by such multiple round-trip passes. Because multiple resonance wavelengths may be tested, multiple species may be detected simultaneously as long as their absorption features fall within the broadband or tunable spectral range of the IR source.

In still other embodiments, which may be combined with one or more of the three approaches described above for reducing losses in the top contact metal, namely making the top contact as laterally narrow as possible, introducing a top cladding layer, and narrowing the top of the ridge, the duty cycle of the contacts along the longitudinal axis of the hybrid waveguide is reduced, as illustrated in FIG. 12D.

In such a case, the hybrid waveguide includes all of the elements described above with respect to FIG. 12C, but rather than patterning a single contact that runs along the entire length of the hybrid waveguide, a series of contact stripes 1250 is formed, with non-contacted regions separating the contact stripes. The contact duty cycle then corresponds to the ratio of the contact length along the longitudinal axis divided by the total period of the contacted plus non-contacted lengths. To minimize losses due to overlap of the optical mode with the contact metal, this duty cycle should be as small as possible while still allowing the detector bias voltage to be applied uniformly and the signal current to be efficiently collected. Using this embodiment, the loss in the metal contact will scale about linearly with the contact duty cycle along the longitudinal axis. In some embodiments, current spreading in the $p^+$ or $n^+$ top contacting layer 1113 or 1113A in FIG. 11A is great enough to allow a relatively low contact duty cycle, e.g., 10-20%, when the longitudinal length of each contact stripe is on the order of 1 μm. A similar approach involving low-duty-cycle top contacts to lower the internal loss was recently applied successfully to interband cascade lasers, which similarly provide considerable current spreading in the layers above the active region of the device (the active gain stages in a laser, by analogy to the absorber region of a detector). See C. D. Merritt, W. W. Bewley, C. L. Canedy, C. S. Kim, M. Kim, M. W. Warren, I. Vurgaftman, and J. R. Meyer, "Distributed-Feedback Interband Cascade Lasers with Reduced Contact Duty Cycles," Proc. SPIE Proc. 9855, 98550C (2016); see also U.S. Pat. No. 9,923,338 to J. R. Meyer, I. Vurgaftman, C. L. Canedy, W. W. Bewley, C. S. Kim, M. Kim, and C. D. Merritt, entitled "Interband Cascade Lasers with Low-Fill-Factor Top Contact for Reduced Loss." As in the case of a laser, it is important to assure that the period of the low-duty-cycle contact does not introduce a parasitic resonance at a wavelength where resonance enhancement is not desired. One approach to avoiding this is to make the spacing of the low-duty-cycle contacts random rather than periodic.

As noted above, tuning the resonance wavelength for absorption by a given chemical species may be achieved by varying the temperature of the sensing area, which may be controlled separately from the temperatures of the source and detection areas. In addition, it will be obvious to one skilled in the art that many other methods for providing sensitivity to the spectroscopic properties of a given gas sample may also be employed in the sensing area of the invention. For example, the cavity may be formed by two mirrors bounding a linear detector pathlength, as discussed above, or by forming a gas cavity somewhere between the source and detection areas of the on-chip sensing system rather than using evanescent coupling to provide overlap of the optical mode with the sample gas.

Figure 13:
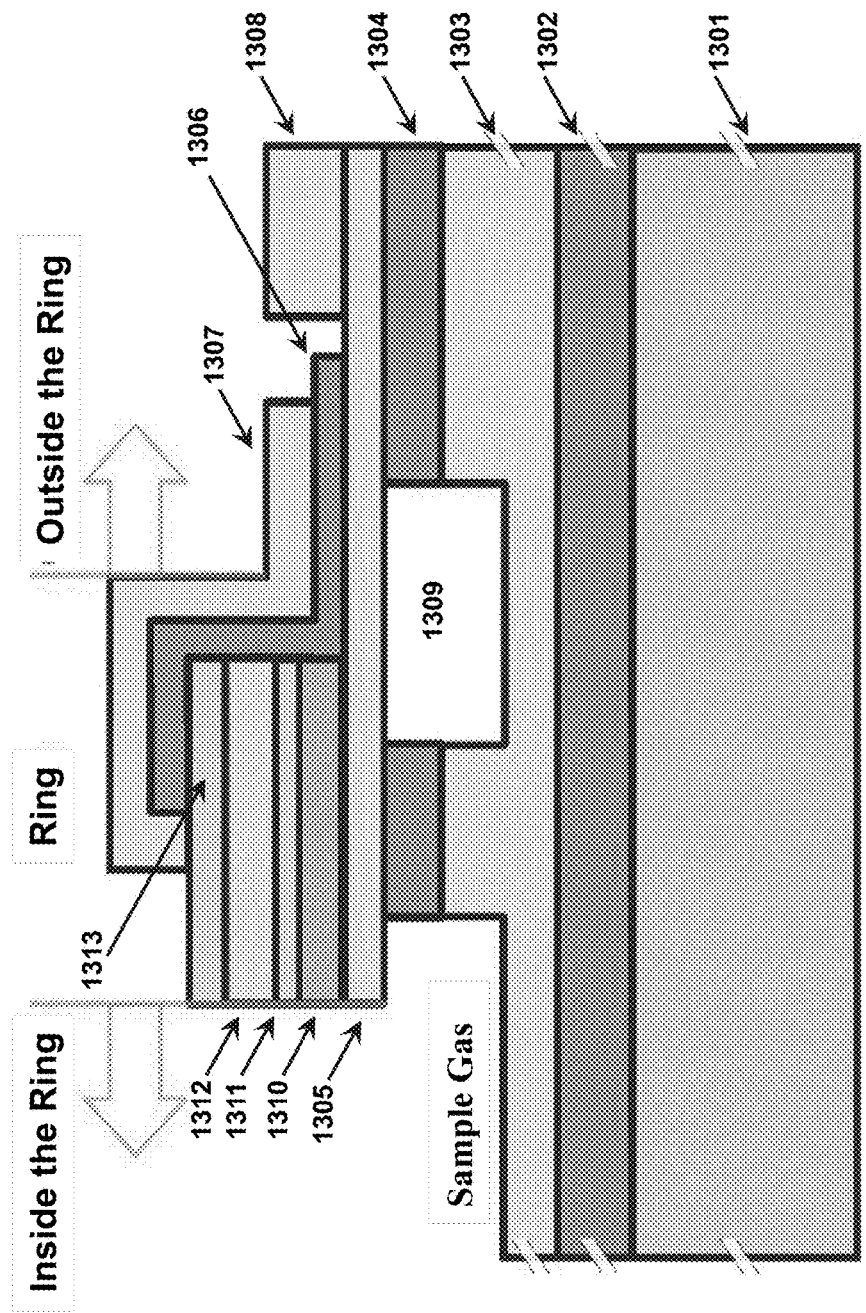
FIG. 13 is a block schematic illustrating an additional exemplary embodiment of a hybrid waveguide that includes a III-V RCID photodiode configured to detect an optical signal propagating along the plane of the epitaxial structure.

The block schematic in FIG. 13 illustrates aspects of an alternative exemplary hybrid waveguide incorporating an RCID photodiode in accordance with the present invention, which can be used in a detector configuration such as that shown in FIG. 14 described below. In this embodiment, an RCID structures for detecting light propagating in the plane resides directly on top of each ring resonator in the sensing area that evanescently couples to the sample gas, so as to form a single hybrid waveguide.

As with the embodiment described above with respect to FIG. 11, the hybrid waveguide is formed when a III-V chip containing the active components of an RCID photodiode is bonded to a pre-processed silicon wafer. In this case, the bonded III-V structure is patterned such that each ring resonator, which is already pre-patterned on the silicon chip before the III-V detector material is bonded, has an RCID structure residing on top of it.

Thus, as illustrated in FIG. 13, a hybrid waveguide in accordance with this embodiment is formed in the ring resonator sensing area of the on-chip sensor rather than on a straight waveguide that is positioned outside the sensing area, as depicted in FIGS. 11A and 11B.

This embodiment further comprises a Si substrate 1301, a first, lower SiN cladding layer 1302, a silicon portion of the core 1303, and an optional SiN second, interposed cladding layer 1304 above the silicon portion of the core. As in the embodiment illustrated in FIG. 11, in this embodiment, the Si 1303 and SiN interposed cladding layer 1304 portions of the waveguide can be patterned to include one or more air or dielectric regions 1309 on each lateral side of the hybrid waveguide to help laterally confine the optical mode propagating in the hybrid waveguide and assure that propagation is in a single lateral mode.

In addition, as with the hybrid waveguide described above with respect to FIG. 11A, the hybrid waveguide depicted in FIG. 13 also includes an RCID photodetector comprising an $n^+$- or $p^+$ bottom contacting layer 1305, an n or p region 1310, a thin active absorber region 1311 (which may employ one of the designs discussed above or some other design), a p or n region 1312, and a $p^+$- or $n^+$ top contact layer 1313.

The waveguide also includes top and bottom metal contact pads 1307/1308. In the embodiment illustrated in FIG. 13, both contact pads are located outside the ring so as to allow the inner surface of the ring to be exposed to the sample gas; however, in other embodiments both contacts may be placed inside the ring while the outer surface is exposed to the sample gas for evanescent coupling to the optical mode. As in the discussion above related to FIG. 11A, as shown in FIG. 13, the top contact metal 1307 should be as narrow as possible to minimize parasitic losses due to overlap of the propagating optical mode with the top contact metal. In addition, as also discussed above, a top cladding layer may be grown above the p-region of the photodiode, the top contacting layer may be grown thicker and then most of it etched to a much narrower width than the rest of the III-V portion of the ridge to suppress penetration of the propagating optical mode into the top contacting metal, and/or a low-duty-cycle top contact may be employed.

Figure 14:
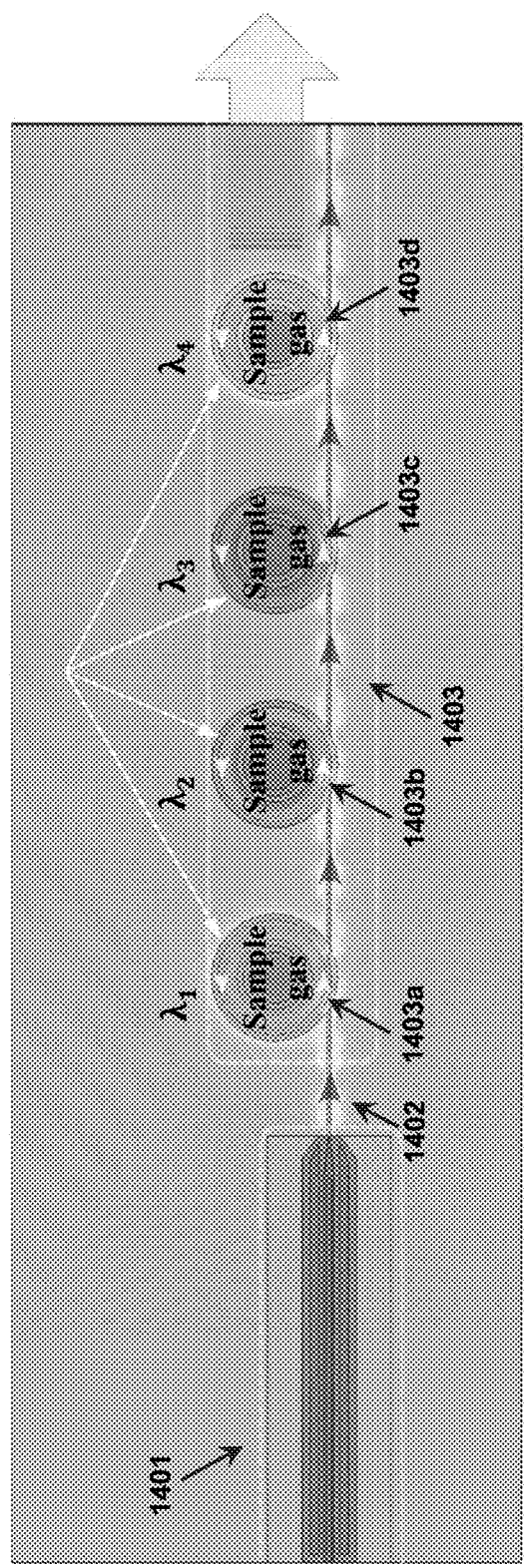
FIG. 14 is a block schematic illustrating aspects of an additional exemplary embodiment of a chemical sensor including a hybrid waveguide incorporating an RCID photodiode configured to detect an optical signal propagating along the plane of the epitaxial structure.

Second, interposed cladding layer 1304 separating the Si portion of the ring resonator waveguide from the III-V detector portion will generally be needed when the detector is incorporated into the ring resonator as shown in FIG. 14; otherwise, optical losses due to coupling of the optical mode propagating in the ring to the absorber layer and $n^+n$-doped bottom contact layer would induce too much absorbance per pass for the ring resonator to maintain a high Q value when the ring diameter is large enough to avoid substantial bending loss. A significant advantage of this embodiment in which the detector is built into the hybrid waveguide of the ring resonator is that no separate tunings of the ring resonance wavelength and RCID resonance wavelength are required to assure that they match, since both will automatically have the same resonance wavelength.

In other "inside-the-ring" embodiments, the RCID can have the structure as illustrated in FIG. 11B, wherein the $p^+$ or $n^+$ top contacting layer is grown to a greater thickness and then etched (down to a depth that still allows sufficient current spreading) to a much narrower ridge width (e.g., 1-2 μm) than the rest of the III-V portion of the hybrid waveguide.

FIG. 14 illustrates aspects of an alternative embodiment of a detector incorporating an in-plane RCID in accordance with the present invention. In the embodiment illustrated in FIG. 14, the ring resonators include the hybrid waveguide illustrated in FIG. 13, with the RCID detectors in each hybrid waveguide (corresponding to RCID detectors 1204a/b/c/d in FIG. 12) residing on top of the ring resonators 1403a/1403b/1403c/1403d, so that the "sensing area" and "detection area" coexist by sharing the same ring resonators formed by the same hybrid waveguides. As a result, in this embodiment, both the sensing cavities and the detector cavities automatically share the same resonance wavelength $\lambda_1, \lambda_2, \lambda_3, \lambda_4$, since they are the same cavity. As with the embodiment illustrated in FIG. 12A, IR output from IR source 1401 propagates through a waveguide 1402 into the ring resonators, where each ring selectively extracts light at its resonance wavelength from the IR source output beam. However, the sample gas resides only inside (or outside) each ring rather than on top as well, since the III-V absorber and contact layers of the detector on top of the ring do not allow access of the gas to the optical mode propagating within the ring.

In some embodiments of the invention, the infrared detector has a majority-carrier barrier configuration with a thin absorber region, i.e., an nBn or pBp configuration such as that discussed above with respect to FIG. 6. In such embodiments, the layers 1310-1313 in FIG. 13 are the appropriate layers known in the art to be used for an nBn or pBp detector, rather than the layers suitable for a photodiode. Detectors with an nBn or pBp configuration are then suitable for use as the detectors that reside on top of the ring resonators in the on-chip sensor that is illustrated schematically in FIG. 14.

A further consideration, for both infrared detectors that are illuminated vertically as well as those that detect light propagating in the plane of the epitaxial layers, is the dark current associated with current leakage at the etched sidewalls that define the individual detecting areas. This parasitic dark current can be especially severe in III-V detectors employing InAs-rich absorber materials such as InAs—Ga(In)Sb and InAs-InAsSb quantum wells or superlattices, as well as the bulk InAsSb alloy, since these materials are prone to a high density of surface states on the exposed etched sidewalls. For a p-type absorber material, these donor-like states induce band bending that results in an electron inversion layer that can cause excessive leakage and detector noise associated with electron conduction along the sidewalls.

Figure 15:
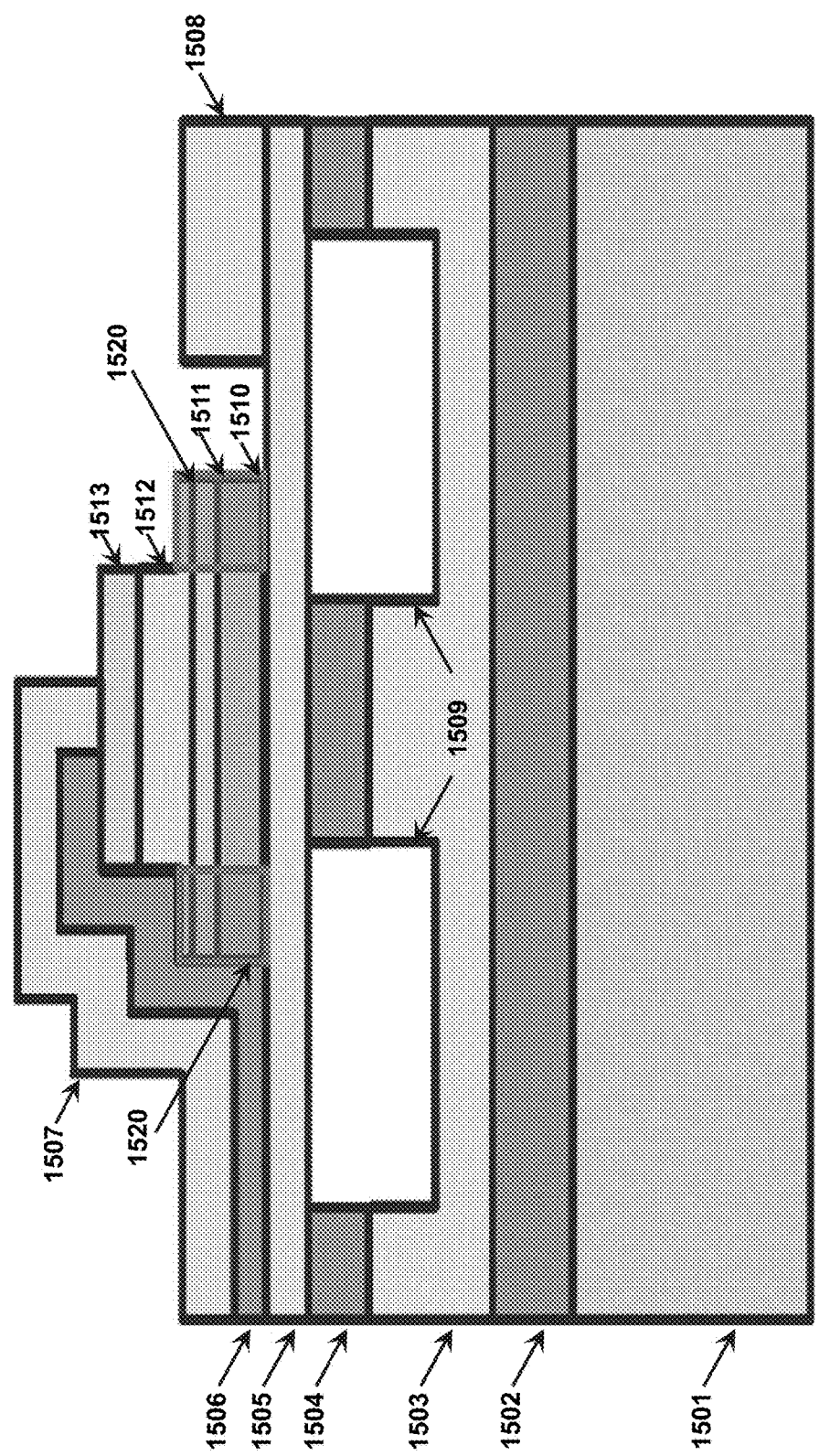
FIG. 15 is a block schematic illustrating an additional exemplary embodiment of a hybrid waveguide incorporating an RCID photodiode in accordance with the present invention, in which portions of the p-region of the waveguide have been ion-bombarded to create an electrical barrier to current flow within the bombarded regions.

FIG. 15 schematically illustrates an embodiment of the invention that will substantially reduce the tendency of a detector designed to detect photons propagating in the plane to display any significant surface leakage. This configuration is analogous to that illustrated in FIG. 11 described above, and so will not be described in detail here for the sake of brevity. However, as described in more detail below, in the embodiment illustrated in FIG. 15, the lateral region of the epitaxial structure near the etched sidewall surfaces is bombarded with ions, for example, protons. Recent unpublished experiments at NRL have demonstrated that bombarding an interband cascade laser (ICL) structure with a sufficient dose of energetic protons can strongly suppress the vertical flow of current through the device. See U.S. Patent Application Publication No. 2017/0373472 to J. R. Meyer, I. Vurgaftman, C. L. Canedy, W. W. Bewley, C. S. Kim, C. D. Merritt, M. V. Warren, and M. Kim, entitled "Weakly Index-Guided Interband Cascade Lasers with No Grown Top Cladding Layer or a Thin Top Cladding Layer." Further unpublished experiments at NRL have shown that, in particular, the current is blocked within the active stages of the ICL rather than the InAs-AlSb superlattice cladding layers or lightly-n-doped GaSb separate confinement layers. These experiments imply that following ion bombardment the electrical resistance in the GaSb hole injector becomes quite large, most likely due to the formation of n-type traps. Since, proton bombardment appears to induce trapping that strongly suppresses the hole transport in GaSb, it may be expected that ion bombardment can also strongly suppress the hole transport in related p-type alloys, such as p-AlGaSb and p-AlGaAsSb.

The embodiment illustrated in FIG. 15 creates an electrical barrier to surface leakage currents by using ion bombardment of both outside edges of the p-region of the III-V structure within the hybrid waveguide to form ion-bombarded regions 1520 adjacent to the etched sidewalls of the p-region, where the ion bombardment strongly suppresses the lateral flow of current into the ion-bombarded regions 1520. The p-regions in this embodiment of the waveguide may be p-GaSb, p-AlGaSb, p-AlGaAsSb, or some other related alloy or a superlattice employing those p-type constituents. Ion bombarding the outside portions of the p-region, e.g., by protons, to form ion-bombarded regions 1520 will block the lateral flow of current from the top contact to the etched sidewalls of the active absorber, whereas the photo-induced signal current flowing from top to bottom in the non-bombarded region is unimpeded. This will strongly suppress dark currents at the surface as a source of noise.

Thus, in accordance with this aspect of the present invention, the outside edges of the p-region of the III-V structure within the hybrid waveguide can be bombarded with ions, e.g., with protons having a predetermined energy and dose, with the extent of the ion bombardment being tailored to provide a predetermined reduction in surface current leakage in the RCID.

FIG. 15 also shows that the bombarded areas of the p⁺-contact layer, along with part of the p-region, may optionally be etched away to further prevent the lateral flow of current to the etched sidewalls of the absorber region. Since very little current will flow through the bombarded regions at both lateral sides of the detector, those bombarded regions may optionally be relatively wide, so as to further prevent current from reaching the sidewalls that may be more conductive. Therefore, there is a trade-off between a narrow width of the bombarded regions to minimize leakage current within the bombarded regions, and a wider width of the bombarded regions to minimize the current that reaches the sidewalls that may be more conductive. A detector with a narrow bombarded region also consumes less real estate in the overall photonic integrated circuit. The introduction of ion bombarded regions 1520 also provides the option of using wet chemical etching to laterally pattern the III-V portion of the device rather than dry etching such as reactive ion etching, since it is no longer critical that the sidewalls be nearly vertical. Surface damage and surface leakage currents are generally lower when wet etching is used rather than dry etching.

Figure 16:
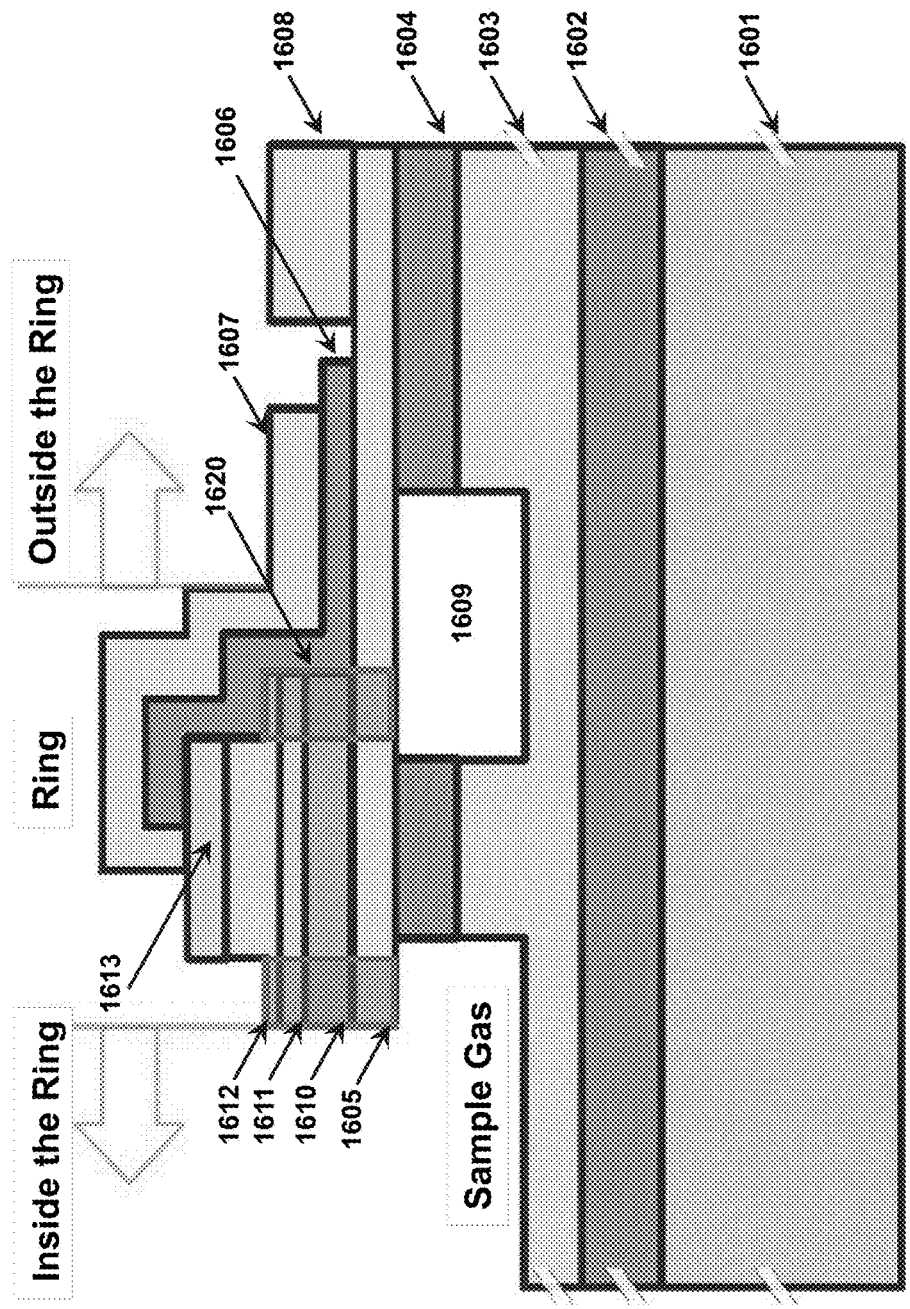
FIG. 16 is a block schematic illustrating an additional exemplary embodiment of a hybrid waveguide incorporating an RCID photodiode in accordance with the present invention, in which portions of the p-region of the waveguide have been ion-bombarded to create an electrical barrier to surface current flow within the bombarded regions.

FIG. 16 shows an embodiment analogous to that illustrated in FIG. 14, except that, as in FIG. 15, the lateral regions near the etched sidewalls of the III-V detector structure are bombarded with ions such as protons to form ion-bombarded regions 1620, which, like the ion-bombarded regions described above with respect to FIG. 15, will strongly suppress leakage currents, particularly at the sidewalls of a detector device that combines the sensing area and the detector in the same resonator as in the embodiment illustrated in FIG. 13.

In some embodiments of the invention, the infrared detector has a majority-carrier barrier configuration with a thin absorber region, i.e., an nBn or pBp configuration such as that discussed above with respect to FIG. 6. In such embodiments, 1510-1513 in FIGS. 15 and 1610-1613 in FIG. 16 are the appropriate layers known in the art to be used for an nBn or pBp detector, rather than the layers suitable for a photodiode.

Ion bombardment can similarly be used to suppress leakage currents at the etched sidewalls of infrared detectors that are photoexcited vertically rather than in the plane of the epitaxial layers. In that case, the introduction of bombarded regions near the etched sidewalls may suppress leakage currents at the sidewalls of a single-element detector, or at the sidewalls of the mesas forming each pixel in an array. Since ion bombardment will strongly suppress any lateral flow of current that would induce cross-talk between neighboring pixels in an array, the individual mesas that form the pixels in the array would no longer need to be defined by a deep etch through the active absorber, but only by a shallow etch that stops in the p-region above the absorber. With no etching through the absorber, sidewall leakage within the individual mesas of the array would be eliminated completely. As in the discussions above related to FIGS. 11 and 13, the top contact metal 1507 in FIGS. 15 and 1607 in FIG. 16 should be as narrow as possible to minimize parasitic losses due to overlap of the propagating optical mode with the top contact metal. In addition, as also discussed above, a top cladding layer may be grown above the p-region of the photodiode, the top contacting layer may be grown thicker and then most of it etched to a much narrower width than the rest of the III-V portion of the ridge to suppress penetration of the propagating optical mode into the top contacating metal, and/or a low-duty-cycle top contact may be employed.

Numerous variations on these inventive embodiments are possible. For example, the IR source can be any suitable IR source, such as a broadband light-emitting device (LED) or amplified spontaneous emission (ASE) device, or a narrow band infrared laser. For example, the source could be an interband cascade light-emitting device (ICLED) such as that described in C. S. Kim et al., "Improved Mid-Infrared Interband Cascade Light Emitting Devices," *Opt. Engr.* 57, 011002 (2018). An ASE source could be provided, for example, by a III-V type-I infrared diode, an interband cascade, or a quantum cascade active gain region whose hybrid waveguide does not provide sufficient feedback to allow lasing. Without feedback, the injection of a current density above the gain threshold will produce output into a relatively broad emission spectrum, but with much higher slope efficiency than an LED operating at the same wavelength. A laser source could be provided by a type-I diode, interband cascade, or quantum cascade laser that employs either a Fabry-Perot cavity to produce multi-mode output (possibly with a spectral intensity profile that is highly irregular and/or unstable), or a distributed feedback (DFB) cavity that provides output in a single spectral mode. Optionally, various methods known to the art may be used to tune the emission wavelength of a single-mode DFB laser. For example, see Okuda et al., supra and Davies et al., supra; see also W. Zhou et al, "Monolithically, widely tunable quantum cascade lasers based on a heterogeneous active region design," *Scientific Reports* 6, 25213 (2016).

In other alternatives, the detector with a thin absorber layer may employ full depletion of its carriers or any of the other designs discussed above. Also, the embodiments illustrated in FIGS. 11 and 14-16 employ an n-region below the absorber region of the RCID photodiode and a p-region above the absorber region, whereas in other embodiments the p-region would be situated below the absorber region and the n-region would be situated above. In other embodiments, the RCID that detects light propagating in the plane would employ an nBn or pBp architecture incorporating a very thin absorber region.

The in-plane waveguide in which the optical signal propagates may be formed entirely within the III-V semiconductor from which the active detector layers are formed, or by bonding to or otherwise combining with some other material to form a hybrid waveguide. Thin quantum well infrared photodetector (QWIP) geometries may be employed in addition to interband absorber configurations, since intersubband absorption is strong for in-plane propagation in the transverse magnetic (TM) polarization. A bolometer detector such as a silicon-based bolometer detector may also be employed. If the hybrid waveguide is silicon-based, several options may be employed for both the core and interposed cladding layers of the silicon-based portion of the waveguide, as long as the resulting waveguide loss is low in the wavelength region of interest. Several methods known to the art are available for forming mirrors that reflect light propagating in the waveguide, and other methods may be employed to form the resonant cavity. Many options are also available for how the in-plane RCID residing in a III-V or hybrid waveguide may be processed.

Various methods may be employed to assure that the emitter wavelength (if its linewidth is narrow), the ring (or other) resonance wavelength in the sensing area, and the RCID wavelength are suitably aligned with the absorption features of the one or more gas species to be sensed. For embodiments in which the emitter has a broad spectral bandwidth (e.g., an LED or ASE device), no tuning of its emission peak is required. Other embodiments may employ a single-mode laser whose emission wavelength can be tuned into resonance with each of the N ring resonators, one at a time, in its turn. In other embodiments, multiple single-mode lasers are combined into a single beam, for example, using an arrayed waveguide grating (AWG) configuration. In still other embodiments, N single-mode lasers may separately inject light into N ring resonators, which either incorporate detectors into each ring or output their signals into N RCIDs.

Advantages and New Features

The central advantage of the invention is that by placing the entire active absorber region of a resonant cavity infrared detector within the depletion region of a p-n junction, the thermal generation noise associated with Auger recombination and impact ionization can be substantially reduced at high operating temperatures and low bias. If Auger-related thermal generation dominates the dark current, this provides a practical means for dramatically reducing the dark-current density at a given operating temperature, or achieving the same dark-current density at a much higher temperature, while providing high detection quantum efficiency within a narrow spectral band of interest.

To minimize the dark current associated with Auger recombination, which generally dominates when conventional broadband MWIR and LWIR photodiodes are operated at sufficiently high temperatures and doping densities, the band alignments between the conduction-band minima and valence-band maxima in the absorber region, n-region, and p-region, should be adjusted according to the specific extrinsic doping level and type, intrinsic carrier concentration, and $\gamma_3^{ppn}/\gamma_3^{nnp}$ ratio for the given device structure at a given operating temperature.

While resonant-cavity photodetectors sensitive to telecom wavelengths ($\lambda$=1.3-1.6 μm) are well known in the prior art, new features of the invention will make it practical for the first time to extend the high performance of resonant cavity detectors to longer wavelengths spanning the SWIR, MWIR, and LWIR bands.

The ultra-thin absorber of the invention substantially reduces dark currents, and also opens the material design space to options that are not feasible using the thick absorber in a conventional broadband IR detector. For example, some embodiments of the invention employ QW configurations that favorably tailor the wavefunction overlap and band alignments, but which cannot be applied to the thick absorbers of conventional detectors because of strain accumulation that induces dislocations. In contrast, the ultra-thin absorber of the invention can tolerate appreciable strain imbalance without compromising material quality, because the absorber is thinner than the critical thickness for the particular layer structure. The ultimate limit is obtained for embodiments of the invention in which the entire absorber region consists of a single type-II interface such as between InAs and GaSb layers.

The RCIDs of the invention will display higher speed and higher operating temperatures than conventional IR detectors. The spectral response can be tuned with an applied bias, by introducing variable spacers or etch depths to vary the resonance wavelengths for multiple detector mesas on the same chip, or with an external position-tunable mirror. The RCID may be monolithically combined with an optical source grown below it on the same chip, and temporal modulation of the optical input can be used to further discriminate against non-optical noise sources.

The discussion above has enumerated a number of alternatives to the exemplary RCID configurations described in the text and figures. Although particular embodiments, aspects, and features have been described and illustrated, one skilled in the art would readily appreciate that the invention described herein is not limited to only those embodiments, aspects, and features but also contemplates any and all modifications and alternative embodiments that are within the spirit and scope of the underlying invention described and claimed herein. The present application contemplates any and all modifications within the spirit and scope of the underlying invention described and claimed herein, and all such modifications and alternative embodiments are deemed to be within the scope and spirit of the present disclosure.

What is claimed is:

1. A hybrid waveguide comprising a III-V resonant-cavity infrared detector (RCID) photodiode ridge integrated with a waveguide, the waveguide comprising:
  a first cladding layer disposed on a substrate;
  a core layer disposed on the first cladding layer; and
  an second cladding layer disposed on the core layer;
the core layer and second cladding layer being patterned to form air or dielectric regions on each lateral side of the hybrid waveguide, the air or dielectric regions being configured to laterally confine light propagating in the waveguide such that propagation is in a single lateral mode;
and the RCID ridge comprising:
  an $n^+$ bottom contact layer disposed on an upper surface of the second cladding layer;
  an n-type region disposed on a first area of an upper surface of the $n^+$ bottom contact layer;
  an absorber region having a thickness of less than 100 nm disposed on an upper surface of the n-type region;
  a p-type region disposed on an upper surface of the absorber layer; and
  a $p^+$ top contact layer;
the hybrid waveguide further comprising a first distributed Bragg reflector (DBR) grating at a first end and a second DBR grating at a second end, the first and second DBR gratings forming a resonant cavity within the RCID photodiode extending along a length of the hybrid waveguide, the resonant cavity having a resonant wavelength $\lambda_R$; and
wherein the RCID photodiode is configured to detect infrared light propagating within the hybrid waveguide, the resonant cavity formed by the first and second DBR gratings being configured to increase an effective absorption path of light having at the resonant wavelength $\lambda_R$ travelling through the hybrid waveguide.

2. The hybrid waveguide according to claim 1, wherein the at least one of the first and second cladding layers is SiN and the core layer is silicon.

3. The hybrid waveguide according to claim 1, wherein the $n^+$ bottom contact layer comprises an $n^+$-InAsSb layer or an $n^+$-InAs/AlSb superlattice.

4. The hybrid waveguide according to claim 1, wherein the n-type region comprises an n-InAs/Al Sb superlattice.

5. The hybrid waveguide according to claim 1, wherein the p-type region comprises p-GaSb or p-AlGaAsSb.

6. The hybrid waveguide according to claim 1, wherein the $p^+$ top contact layer comprises $p^+$-GaSb or $p^+$-AlGaAsSb.

7. The hybrid waveguide according to claim 1, wherein at least one outside edge of the p-layer is ion-bombarded to form at least one ion-bombardment region having a predetermined extent of ion bombardment, the extent of ion bombardment being tailored to provide a predetermined reduction in surface current leakage in the RCID.

8. The hybrid waveguide in accordance to claim 1, wherein the top metal contact is much narrower laterally than the top of the RCID ridge.

9. The hybrid waveguide according to claim 1, wherein the p+ top contact layer has a lateral width configured to minimize parasitic losses resulting from overlap of the propagating optical mode with the top contact metal.

10. The hybrid waveguide according to claim 1, further comprising a top cladding layer having a low refractive index disposed between the p-type region and the p+ top contact layer, the top cladding layer being configured to minimize mode penetration into the top contact metal.

11. The hybrid waveguide according to claim 1, wherein the p+ top contact layer is patterned along its longitudinal axis into a series of alternating contact stripes and non-contacted regions to provide a low-duty cycle top electrical contact.

* * * * *